United States Patent [19]
Clemence et al.

[11] Patent Number: 5,985,894
[45] Date of Patent: Nov. 16, 1999

[54] N-SUBSTITUTED QUINOLINES

[75] Inventors: François Clemence; Michel Fortin, both of Paris; Jean-Luc Haesslein, Courtry, all of France

[73] Assignee: Hoechst Marion Roussel, France

[21] Appl. No.: 08/964,182

[22] Filed: Nov. 4, 1997

Related U.S. Application Data

[63] Continuation of application No. 08/196,424, Feb. 15, 1994, abandoned, which is a continuation of application No. 07/832,030, Feb. 6, 1992, abandoned.

[30] Foreign Application Priority Data

Feb. 7, 1991 [FR] France ................................. 91 01372
Aug. 20, 1991 [FR] France ................................. 91 10433
Nov. 20, 1991 [FR] France ................................. 91 14282

[51] Int. Cl.$^6$ ...................... A61K 31/47; C07D 215/233
[52] U.S. Cl. ............................................. 514/312; 546/153
[58] Field of Search .............................. 546/153; 514/312

[56] References Cited

U.S. PATENT DOCUMENTS

| | | | |
|---|---|---|---|
| 2,555,943 | 6/1951 | Surrey ....................... | 546/156 |
| 3,002,001 | 9/1961 | Surrey ....................... | 546/153 |
| 4,918,081 | 4/1990 | Huang et al. ............... | 514/311 |
| 4,920,131 | 4/1990 | Huang et al. ............... | 514/311 |
| 4,959,363 | 9/1990 | Wentland .................... | 546/153 |
| 5,064,825 | 11/1991 | Chakravarty et al. ........ | 540/490 |
| 5,157,040 | 10/1992 | Greenlee et al. ............. | 546/153 |
| 5,162,325 | 11/1992 | Chakravarty et al. ........ | 514/253 |
| 5,162,340 | 11/1992 | Chakravarty et al. ........ | 514/253 |
| 5,304,565 | 4/1994 | Morimoto ................... | 514/312 |

FOREIGN PATENT DOCUMENTS

| | | |
|---|---|---|
| 343574 | 11/1989 | European Pat. Off. . |
| 412848 | 2/1991 | European Pat. Off. . |

OTHER PUBLICATIONS

Roberts et al., *Chem Abstr* vol. 115 Entry 71607 g (1990) abstracting EP412848.
Zhou et al. Chem. Abstr. vol. 114 entry 206981b (1990).
Tamada et al. Chem.Abstr vol. 111 Entry 194610c (1989).
Baker et al. J. Med. Chem. vol. 15, p. 233–5 (1972).
Coppola, Chem Abstr vol. 100 Entry 156472 (1983).
Berlot, Chem. Abstr vol. 86 Entry 43535 (1976).

*Primary Examiner*—Richard L. Raymond
*Attorney, Agent, or Firm*—Bierman, Muserlian and Lucas

[57] ABSTRACT

Novel N-substituted quinolines of the formula $I_D$ wherein is or useful in the treatment of cardiovascular illnesses having an alteration in the vasomotricity and a process for their preparation.

7 Claims, No Drawings

N-SUBSTITUTED QUINOLINES

PRIOR APPLICATIONS

This application is a continuation of U.S. patent application Ser. No. 08/196,424 filed Feb. 15, 1994, now abandoned, which is a continuation of U.S. patent application Ser. No. 07/832,030 filed Feb. 6, 1992, now abandoned.

STATE OF THE ART

Related prior art includes Bulletin of the Chemical Society of Japan, Vol. 46 No. 2, p. 530 to 534, Chem. Abs., Vol. 85 (1976), p. 466 No. 45850y and Vol. 111 (1989), p.758, No. 194610C, Journal of Medicinal Chemistry, Vol. 15, No. 3, p. 230 to 235 and U.S. Pat. No. 4,711,898, U.S. Pat. No. 4,302,460, U.S. Pat. No. 3,933,818 and U.S. Pat. No. 4,187,310 and British Patents No. 1,472,767 and No. 1,419,788.

OBJECTS OF THE INVENTION

It is an object of the invention to provide the novel compounds of formula $I_D$ and their non-toxic, pharmaceutically acceptable salts with acids and bases and a process for their preparation.

It is another object of the invention to provide novel compositions and method for treating cardiovascular illnesses.

These and other objects and advantages of the invention will become obvious from the following detailed description.

THE INVENTION

The novel compounds of the invention are selected from the group consisting of all possible racemic, enantiomeric and diastereoisomeric forms of a compound of the formula $I_D$

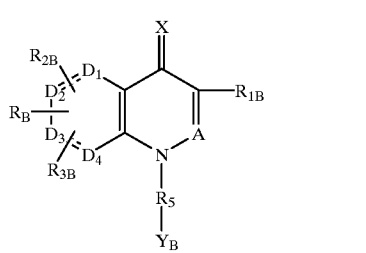

wherein

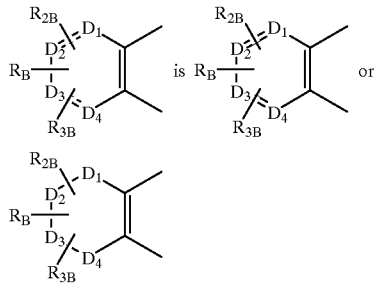

$D_1$, $D_2$, $D_3$ and $D_4$ are individually selected from the group consisting of nitrogen, methine and methylene all optionally substituted with a member of the group consisting of $R_B$, $R_{2B}$, and $R_{3B}$ with at most 2 of $D_1$, $D_2$, $D_3$ and $D_4$ being nitrogen, $R_{1B}$ is selected from the group consisting of hydrogen, alkyl, alkenyl and alkynyl of up to 6 carbon atoms and cycloalkyl of 3 to 7 carbon atoms, all optionally substituted, acyl, —CN and free, salified, esterified or amidified carboxy, $R_B$, $R_{2B}$ and $R_{3B}$ are individually selected from the group consisting of a) hydrogen, halogen, —OH, —SH, —CN, —NO$_2$, sulfo, benzoyl, formyl, acyl and acyloxy of up to 12 carbon atoms, free, salified or esterified carboxy, cycloalkyl of 3 to 7 carbon atoms, b) alkyl, alkenyl, alkynyl, alkoxy and alkylthio of up to 6 carbon atoms and optionally substituted, c) aryl, aralkyl, aralkenyl, aryloxy and arylthio with up to 6 alkyl or alkenyl carbon atoms, the aryl, aralkyl, aralkenyl and aralkylthio being a monocyclic of 5 or 6 members or a condensed ring of 8 to 10 ring members, both optionally containing at least one oxygen, sulfur or nitrogen atom and optionally substituted, d) a member of the group consisting of

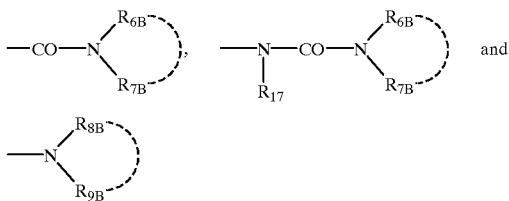

wherein $R_{17}$, $R_{6B}$ and $R_{7B}$ or $R_{8B}$ and $R_{9B}$ individually are selected from the group consisting of hydrogen, free, salified, esterified or amidified carboxy, alkyl and alkenyl of up to 6 carbon atoms optionally substituted with at least one member of the group consisting of halogen, —OH and alkoxy of 1 to 6 carbon atoms, aryl and aralkyl with 1 to 6 alkyl carbon atoms and the aryl is a monocyclic of 5 to 6 ring members and condensed rings of 8 to 10 ring members optionally containing at least one oxygen, sulfur or nitrogen and optionally substituted by at least one member of the group consisting of halogen, —OH, —CN, —CF$_3$, —NO$_2$, alkyl, alkenyl, alkoxy, alkylthio and acyl of up to 6 carbon atoms and free, salified or esterified carboxy and —(CH$_2$)$_{m1}$—S(O)$_{m2}$—Z—R$_{14}$, $m_1$ is an integer from 2 to 4, $m_2$ is an integer from 0 to 2, either Z—R$_{14}$ is —NH$_2$ or Z is selected from the group consisting of

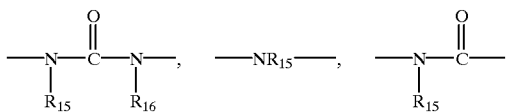

and a single bond, $R_{14}$ is alkyl, alkenyl, alkoxy or aryl optionally substituted, $R_{15}$ and $R_{16}$ being hydrogen or $R_{14}$ or $R_{6B}$ and $R_{7B}$ or $R_{8B}$ and $R_{9B}$ together with the nitrogen to which they are attached form a monocycle of 5 to 6 ring members or condensed rings of 8 to 10 ring members optionally containing at least one oxygen, sulfur or nitrogen and optionally substituted with at least one member of the group consisting of halogen, —OH, —CN, —CF$_3$, —NO$_2$, alkyl, alkenyl, alkoxy and alkylthio of up to 6 carbon atoms and free, salified or esterified carboxy or $R_{8B}$ and $R_{9B}$ individually or one of $R_{6B}$ or $R_{7B}$ is acyl of an organic crboxylic acid of up to 6 carbon atoms and e) —(CH$_2$)$_{m1}$—S(O)$_{m2}$—Z'—R'$_{14}$, $m_1$ and $m_2$ having the above definitions so that when $m_1$ is other than 0, —Z'—R'$_{14}$ is an amino optionally substituted with a alkyl or alkenyl of up to 6 carbon atoms and phenyl, all optionally substituted with at least one member of the group consisting of halogen, —OH, —CF$_3$, —CN, alkyl and alkoxy of 1 to 4 carbon atoms, tetrazolyl and free, salified or esterified carboxy or whatever $m_1$ is, R'$_{14}$ is selected from the group consisting of alkyl and alkenyl of up to 6 carbon atoms and aryl, all optionally substituted with at least one member of the group consisting of halogen, —OH, —CF$_3$, —CN, alkyl and alkoxy of 1 to 4 carbon atoms, tetrazolyl and free, salified, esterified or amidified carboxy and Z' is selected from the group consisting of a single bond, —N(R'$_{15}$)—,

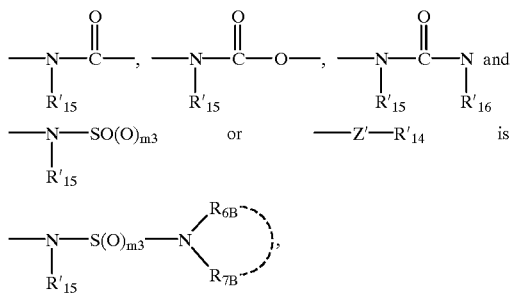

R'$_{15}$ and R'$_{16}$ are individually hydrogen or R'$_{14}$, m$_3$ is an integer from 0 to 2 and R$_{6B}$ and R$_{7B}$ have the above definitions, X is oxygen or sulfur, A is nitrogen or —CR$_4$ and R$_4$ is R$_{1B}$ with the proviso that when A is nitrogen or —CH—, R$_{1B}$ is not hydrogen, R$_5$ is a divalent alkylene of 1 to 4 carbon atoms, Y$_B$ is —Y$_{1B}$—B—Y$_{2B}$, Y$_{1B}$ is a monocyclic aryl of 5 to 6 ring members or condensed rings of 8 to 10 ring members optionally containing at least one oxygen, sulfur or nitrogen in the ring and optionally substituted with at least one substituent selected from the definitions of R$_B$, R$_{2B}$ or R$_{3B}$, B is a single bond between Y$_{1B}$ and Y$_{2B}$ or is selected from the group consisting of

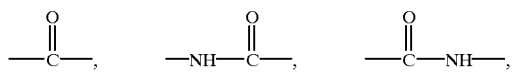

—O—(CH$_2$)$_n$— and —S—(CH$_2$)$_n$—, n is an integer from 0 to 4, when B is a single bond, Y$_{2B}$ is selected from the group consisting of hydrogen, halogen, —OH, —CN, —NO$_2$, —CF$_3$, tetrazole, isoxazole and free, salified and esterified carboxy and when B is other than a single bond, Y$_{2B}$ has the definition of Y$_{1B}$ excluding the compounds of formula I$_D$ wherein

wherein R$_B$ is hydrogen, D$_1$, D$_2$, D$_3$ and D$_4$ are methine, X is oxygen and either A is CH substituted by a methyl substituted by free or esterified carboxy, R$_{1B}$, R$_{2B}$ and R$_{3B}$ are hydrogen and —R$_5$—Y$_B$ is fluorobenzyl or A is CH and R$_{1B}$, R$_{2B}$ and R$_{3B}$ are methyl and —R$_5$—Y$_B$ is benzyl or A is a nitrogen, R$_{1B}$ is ethyl substituted by a free or esterified carboxy, cyano or carbamoyl, one of R$_{2B}$ and R$_{3B}$ is hydrogen and the other is alkyl, alkoxy or phenyl and —R$_5$—Y$_B$ is benzyl optionally substituted with alkyl, alkoxy or phenyl or Y$_{1B}$ is

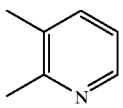

and either A is methine substituted with alkyl and R$_{1B}$ is hydrogen or A is methine and R$_{1B}$ is alkyl, R$_5$ is —CH$_2$— and Y$_B$ is a biphenyl substituted in the ortho position on the ring not attached to R$_5$ with carboxy or tetrazolyl and their non-toxic, pharmaceutically acceptable salts with acids and bases.

Among the preferred compounds of formula I$_D$ are those of the formula

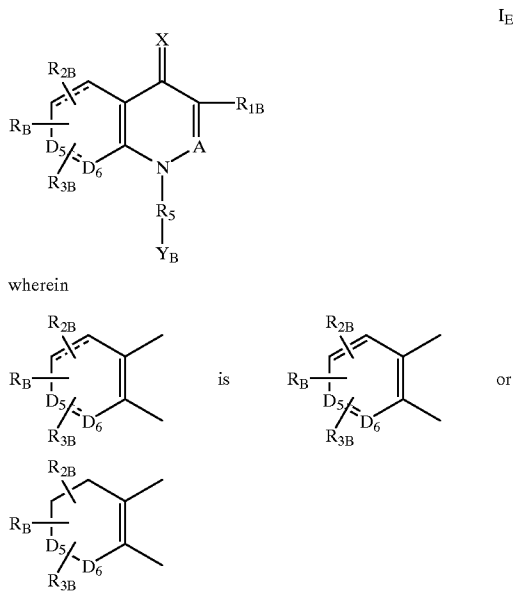

D$_5$ and D$_6$ individually are selected from the group consisting of nitrogen, methine and methylene optionally substituted with R$_B$, R$_{2B}$ or R$_{3B}$ at least one of D$_5$ and D$_6$ being nitrogen, R$_{1B}$ is selected from the group consisting of hydrogen, alkyl, alkenyl and alkynyl of up to 6 carbon atoms and cycloalkyl of 3 to 7 carbon atoms, all optionally substituted, acyl, —CN and free, salified, esterified or amidified carboxy, R$_B$, R$_{2B}$ and R$_{3B}$ are individually selected from the group consisting of a) hydrogen, —OH, —SH, —CN, —NO$_2$, sulfo, formyl, benzoyl, acyl and acyloxy of up 12 carbon atoms, cycloalkyl of 3 to 7 carbon atom and free, salified and esterified carboxy, b) alkyl, alkenyl, alkynyl, alkoxy and alkylthio of up to 6 carbon atoms optionally substituted, c) aryl aralkyl, aralkenyl, aryloxy and arylthio with up to 6 alkyl or alkenyl carbon atoms, the aryl portion being a monocycle of 5 to 6 ring members or condensed rings of 8 to 10 ring members optionally containing at least one nitrogen, oxygen or sulfur as a ring member and optionally substituted, d)

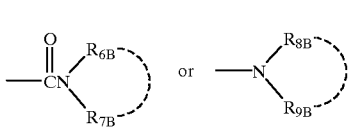

wherein R$_{6B}$ and R$_{7B}$ or R$_{8B}$ and R$_{9B}$ are individually selected from the group consisting of hydrogen, alkyl and alkenyl of up to 6 carbon atoms optionally substituted with at least one halogen or hydroxyl, alkyl and alkenyl of 2 to 6 carbon atoms substituted with alkoxy of 1 to 6 carbon atoms, aryl or aralkyl with 1 to 6 alkyl carbon atoms and the aryl moiety being a monocycle of 5 to 6 ring members or condensed rings of 8 to 10 ring members, the rings optionally containing at least one oxygen, nitrogen or sulfur and optionally substituted with at least one member of the group consisting of halogen, —OH, —CN, —CF$_3$, —NO$_2$, alkyl, alkenyl, alkoxy, alkylthio and acyl of up to 6 carbon atoms and free, salified or esterified carboxy, —(CH$_2$)$_{m1}$—S(O)$_{m2}$—Z—R$_{14}$, m$_1$ is an integer from 0 to 4, m$_2$ is an integer from 0 to 2 and either —Z—R$_{14}$ is —NH$_2$ or Z is selected from the group consisting of

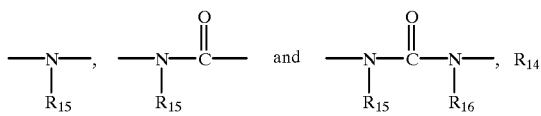

is optionally substituted alkyl, alkenyl or aryl, R$_{15}$ and R$_{16}$ are individually hydrogen, or R$_{14}$, or R$_{6B}$ and R$_{7B}$ or R$_{8B}$ and R$_{9B}$ together with the nitrogen to which they are attached form a monocycle of 5 to 6 ring members or condensed rings of 8 to 10 ring members optionally containing as a ring member at least one nitrogen, oxygen or sulfur and optionally substituted with at least one member of the group consisting of halogen, —OH, —CN, —CF$_3$, —NO$_2$, free, salified and esterified carboxy and alkyl, alkenyl, alkoxy, alkylthio and acyl of up to 6 carbon atoms or R$_{8B}$ and R$_{9B}$ individually or one of R$_{6B}$ or R$_{7B}$ is acyl of an organic carboxylic acid of up to 6 carbon atoms, e) —(CH$_2$)$_{m1}$—S(O)$_{m2}$—Z—R$_{14}$ as defined above, X is oxygen or sulfur, A is nitrogen or —CR$_4$, R$_4$ has the value of R$_{1B}$ with the proviso that it is not hydrogen when A is nitrogen or CH, R$_5$ is a divalent alkylene of 1 to 4 carbon atoms, Y$_B$ is —Y$_{1B}$—B—Y$_{2B}$, Y$_{1B}$ is monocyclic aryl of 5 to 6 ring members or condensed rings of 8 to 10 ring members optionally containing at least one ring member nitrogen, sulfur or oxygen and optionally substituted by at least one member of the group consisting of R$_B$, R$_{2B}$ and R$_{3B}$, B is selected from the group consisting of a single bond,

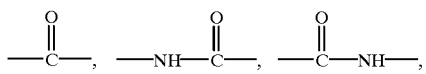

—O—(CH$_2$)$_n$— and —S—(CH$_2$)$_n$— n is an integer from 0 to 4, Y$_{2B}$ when B is a single bond is selected from the group consisting of hydrogen, halogen, —OH, —CN, —NO$_2$, —CF$_3$, tetrazole, isoxazole and free, salifieid and esterified carboxy and Y$_{2B}$ has the value of Y$_{1B}$ when B is other than a single bond.

When D$_1$, D$_2$, D$_3$, D$_4$, D$_5$ or D$_6$ is —NR$_B$, —NR$_{2B}$ or —NR$_{3B}$, R$_B$, R$_{2B}$ and R$_{3B}$ are preferably not chosen from halogen, mercapto, cyano, nitro, sulfo, carboxy and acyloxy.

Another preferred group of compounds of the invention are compounds having the formula

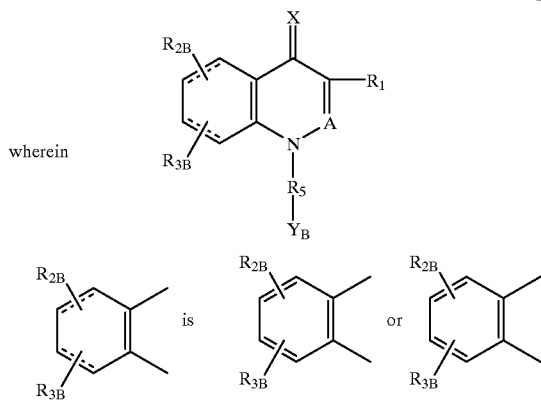

R$_1$ is selected from the group consisting of hydrogen, alkyl, alkenyl and alkynyl of up to 6 carbon atoms and optionally substituted, acyl, —CN and free, salified and esterified carboxy, R$_{2B}$ and R$_{3B}$ are individually selected from the group consisting of a) hydrogen, halogen, —OH, —SH, —CN, —NO$_2$, sulfo, formyl, benzoyl, acyl and acyloxy of up to 12 carbon atoms, cycloalkyl of 3 to 7 carbon atoms and free, salified and esterified carboxy, b) alkyl, alkenyl, alkynyl, alkoxy and alkylthio of up to 6 carbon atoms and optionally substituted, c) aryl, aralkyl, aralkenyl, aryloxy and arylthio with up to 6 alkyl or alkenyl carbon atoms, the aryl moiety being a monocyclic of 5 to 6 ring members or condensed rings of 8 to 10 rings members optionally containing at least one ring member oxygen, nitrogen or sulfur and optionally substituted, d)

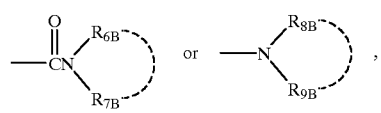

R$_{6B}$ and R$_{7B}$ or R$_{8B}$ and R$_{9B}$ are individually selected from the group consisting of hydrogen, alkyl and alkenyl of up to 6 carbon atoms optionally substituted with at least one hydroxy or halogen, alkyl and alkenyl of 2 to 6 carbon atoms substituted by alkoxy of 1 to 6 carbon atoms, aryl or aralkyl with 1 to 6 alkyl carbon atoms and the aryl moiety being a monocyclic of 5 to 6 ring members or condensed rings of 8 to 10 ring members optionally containing at least one ring member oxygen, sulfur or nitrogen and optionally substituted with at least one member of the group consisting of halogen, —OH, —CN, —CF$_3$, —NO$_2$, alkyl, alkenyl, alkoxy, alkylthio and acyl of up to 6 carbon atoms and free, salified and esterified carboxy, or —(CH$_2$)$_{m1}$—S(O)$_{m2}$—Z—R$_{14}$, m$_1$ is an integer from 0 to 4, m$_2$ is an integer from 0 to 2, either —Z—R$_{14}$ is —NH$_2$ or Z is selected from the group consisting of a single bond,

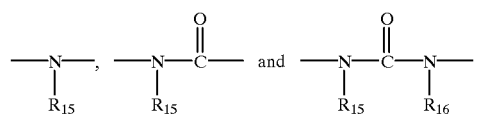

and R$_{14}$ is optionally substituted alkyl, alkenyl or aryl, R$_{15}$ and R$_{16}$ are individually hydrogen or have the value of R$_{14}$ or R$_{6B}$ and R$_{7B}$ or R$_{8B}$ and R$_{9B}$ together with the nitrogen to which they are attached form a monocyclic of 5 to 6 ring members or condensed rings of 8 to 10 ring members optionally containing as at least one ring member oxygen, nitrogen or sulfur and optionally substituted with at least one member of the group consisting of halogen, —OH, —CN, —CF$_3$, —NO$_2$, alkykl, alkenyl, alkoxy, alkylthio and acyl of up to 6 carbon atoms and free, salified and esterified carboxy or R$_B$ and R$_{9B}$ are individually or one of R$_{6B}$ or R$_{7B}$ is acyl of a carboxylic acid of up to 6 carbon atoms, e) —(CH$_2$)$_{m1}$—S(O)$_{m2}$—Z—R$_{14}$ as defined above, X is oxygen or sulfur, a is nitrogen or CR$_4$, R$_4$ has the value of R$_1$ with the proviso that R$_1$ is not hydrogen when A is nitrogen or CH, R$_5$ is a divalent alkylene of 1 to 4 carbon atoms, Y$_B$ is —Y$_{1B}$—B—Y$_{2B}$, Y$_{1B}$ is a monocyclic aryl of 5 to 6 ring members or condensed rings of 8 to 10 ring members optionally containing at least one ring member oxygen, nitrogen or sulfur and optionally substituted by at least one of the values of R$_{2B}$ or R$_{3B}$, B is selected from the group consisting of a single bond,

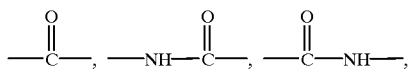

—O—(CH$_2$)$_n$— and —S—(CH$_2$)$_n$—, n is an integer from 0 to 4, Y$_{2B}$ if B is a single bond is selected from the group consisting of hydrogen, halogen, —OH, —CN, —NO$_2$, —CF$_3$, tetrazole, isoxazole and free, salified or esterified carboxy or Y$_{2B}$ if B is other than a single bond has the value of Y$_{1B}$ except the compounds wherein

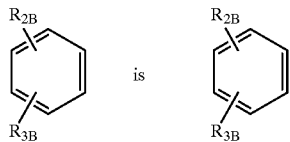

X is oxygen and either A is CH substituted by methyl optionally substituted with free or esterified carboxy, and R$_1$, R$_{2B}$ and R$_{3B}$ are hydrogen and —R$_5$—Y$_B$ is fluorobenzyl or A is CH, R$_1$, R$_{2B}$ and R$_{3B}$ are methyl and —R$_5$—Y$_B$ is benzyl or A is nitrogen, R$_1$ is ethyl substituted with free or esterified carboxy or —CN or carbamoyl, one of R$_{2B}$ and R$_{3B}$ is hydrogen and the other is alkyl or alkoxy or phenyl and —R$_5$—Y$_B$ is benzyl optionally substituted by alkyl or alkoxy or phenyl.

A more preferred group of compounds of the invention are compounds having the formula

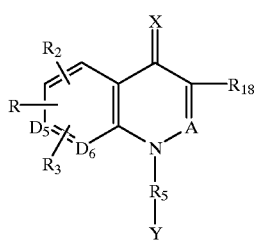

I$_G$ wherein D$_5$ and D$_6$ are individually are nitrogen or CH optionally substituted by R or R$_2$ or R$_3$, R$_{1B}$ is selected from the group consisting of hydrogen, alkyl, alkenyl and alkynyl of up to 6 carbon atoms and cycloalkyl of 3 to 7 carbon atoms, all optionally substituted, acyl, —CN and free, salified, esterified or amidified carboxy, R, R$_2$ and R$_3$ are individually selected from the group consisting of a)

hydrogen, halogen, —OH, —CN, —SH, —NO$_2$, sulfo, formyl, benzoyl, acyl of up to 12 carbon atoms, cycloalkyl of 3 to 7 carbon atoms and free, salified or esterified carboxy, b) alkyl, alkenyl, alkynyl, alkoxy and alkylthio of up to 6 carbon atoms and optionally substituted, c) aryl, aralkyl, aralkenyl, aryloxy and arylthio of up to 6 alkyl or alkenyl carbon atoms and the aryl moiety is a monocyclic aryl of 5 to 6 ring members or condensed rings of 8 to 10 ring members optionally containing at least one ring member oxygen, nitrogen or sulfur and optionally substituted,

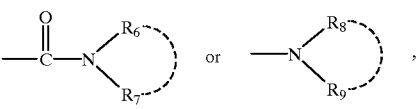

R$_6$ and R$_7$ and R$_8$ R$_9$ are individually selected from the group consisting of hydrogen, alkyl and alkenyl of up to 6 carbon atoms optionally substituted with at least one halogen or hydroxyl, alkyl and alkenyl of 2 to 6 carbon atoms substituted with alkoxy of 1 to 6 carbon atoms, aryl and aralkyl with 1 to 6 alkyl carbon atoms, the aryl being a monocyclic aryl of 5 to 6 ring members or condensed rings of 8 to 10 ring members optionally containing at least one ring member of nitrogen, oxygen and sulfur and optionally substituted with at least one member of the group consisting of halogen, —OH, —CN, —CF$_3$, —NO$_2$, alkyl, alkenyl, alkoxy, alkylthio and acyl of up to 6 carbon atoms and free, salified and esterified carboxy or R$_6$ and R$_7$ or R$_8$ and R$_9$ together with the nitrogen to which they are attached form a monocycle of 5 to 6 ring members or condensed rings of 8 to 10 rings members optionally containing at least one ring member being nitrogen, sulfur or oxygen and optionally substituted with at least one member of the group consisting of halogen, —OH, —CN, —CF$_3$, —NO$_2$, alkyl, alkenyl, alkoxy, alkylthio and acyl of up to 6 carbon atoms and free, salified and esterified carboxy or R$_8$ and R$_9$ individually or R$_6$ or R$_5$ are acyl of a carboxylic acid of 1 to 6 carbon atoms, X is oxygen or sulfur, A is nitrogen or C—R$_4$, R$_4$ has the value of R$_{1B}$ with the proviso R$_4$ is not hydrogen when A is nitrogen or CH, R$_5$ is alkylene of up to 4 carbon atoms, Y is —Y$_1$—B—Y$_2$, Y$_1$ is monocyclic aryl of 5 to 6 ring members or condensed rings of 8 to 10 ring members optionally containing at least one ring member oxygen, nitrogen or sulfur and optionally substituted with at least one of R, R$_2$ and R$_3$, B is selected from the group consisting of a single bond,

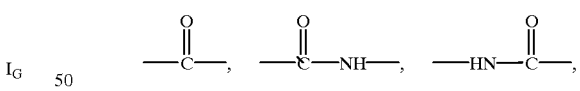

—O—(CH$_2$)$_n$— and —S—(CH$_2$)$_n$—, n is an integer from 0 to 4, Y$_2$ when B is a sing bond is selected from the group consisting of hydrogen, halogen, —OH, —CN, —NO$_2$, —CF$_3$, tetrazole, isoxazole and free, salified and esterified carboxy or Y$_2$ if B is other than a single bond has the value of Y$_1$ except the compounds wherein X is oxygen, D$_5$ and D$_6$ are methine, R is hydrogen and either A is CH substituted by methyl optionally substituted by free or esterified carboxy, R$_1$, R$_2$ and R$_3$ are hydrogen and —R$_5$—Y is fluorobenzyl or A is CH, R$_1$, R$_2$ and R$_3$ are methyl and —R$_5$—Y is benzyl or A is nitrogen, R$_1$ is ethyl substituted by free or esterified carboxy, one of R$_2$ and R$_3$ is hydrogen and the other is alkyl or alkoxy or phenyl and —R$_5$—Y is benzyl optionally substituted with alkyl or alkoxy or phenyl.

Another preferred group of compounds of the invention are compounds of the formula

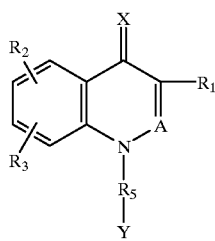

wherein R₁ is selected from the group consisting of hydrogen, alkyl, alkenyl and alkynyl of up to 6 carbon atoms and optionally substituted, acyl, —CN and free, salified and esterified carboxy, R₂ and R₃ are individually a) hydrogen, halogen, —OH, —SH, —CN, —NO₂, sulfo, formyl, benzoyl, acyl of up to 12 carbon atoms, cycloalkyl of 3 to 7 carbon atoms and free, salified and esterified carboxy, b) alkyl, alkenyl, alkynyl, alkoxy and alkylthio of up to 6 carbon atoms and optionally substituted, c) aryl, aralkyl, aralkenyl, aryloxy and arylthio with up to 6 alkyl or alkenyl carbon atoms and the aryl is a monocycle of 5 to 6 ring members or condensed rings of 8 to 10 carbon atoms optionally containing at least one ring member oxygen, nitrogen or sulfur and optionally substituted, d)

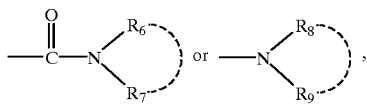

either R₆ and R₇ or R₈ and R₉ are individually selected from the group consisting of hydrogen, alkyl and alkenyl of up to 6 carbon atoms optionally substituted with at least one halogen or —OH, alkyl and alkenyl of 2 to 6 carbon atoms substituted with alkoxy of 1 to 6 carbon atoms, aryl and aralkyl of 1 to 6 alkyl carbon atoms and the aryl moiety is monocyclic of 5 to 6 ring members or condensed rings of 8 to 10 carbon atoms optionally containing at least one ring member oxygen, nitrogen or sulfur and optionally substituted with at least one member of the group consisting of halogen, —OH, —CN, —CF₃, —NO₂, alkyl, alkoxy, alkylthio and acyl of up to 6 carbon atoms and free, salified or esterified carboxy or R₆ and R₇ or R₈ and R₉ together with the nitrogen to which they are attached form a monocyclic of 5 to 6 ring members or condensed rings of 8 to 10 ring members and optionally containing at least one ring member oxygen, nitrogen or sulfur and optionally substituted with at least one member of the group consisting of halogen, —OH, —CN, —CF₃, —NO₂, alkyl, alkenyl, alkoxy and alkylthio of up to 6 carbon atoms and free, salified and esterified carboxy, or R₈ and R₉ individually and one of R₆ or R₇ is acyl of a carboxylic acid of up to 6 carbon atoms, A is nitrogen or CR₄, R₄ has the value of R₁ with the proviso that R₄ is not hydrogen when A is nitrogen or CH. R₅ is alkylene of 1 to 4 carbon atoms, Y is —Y₁—B—Y₂, Y₁ is a monocyclic aryl of 5 to 6 ring members or condensed rings of 8 to 10 ring members optionally containing at least one ring member oxygen, nitrogen or sulfur and optionally substituted by at least one of R₂ or R₃, B is selected from the group consisting of a single bond,

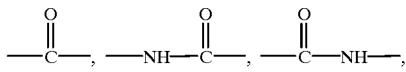

—O—(CH₂)ₙ— and S—(CH₂)ₙ—, n is an integer from 0 to 4, Y₂ is when B is a single bond is selected from the group consisting of hydrogen, halogen, —OH, —CN, —NO₂, —CF₃, tetrazole, isoxazole and free, salified and esterified carboxy except the compounds wherein X is hydrogen and either A is CH substituterd by methyl optionally substituted by free or esterified carboxy, R₁, R₂ and R₃ are hydrogen and —R₅—Y is fluorobenzyl or A is CH, R₁, R₂ and R₃ are methyl and —R₅—Y is benzyl or A is nitrogen, R₁ is ethyl substituted by free or esterified carboxy, one of R₂ and R₃ is hydrogen and the other is alkyl, alkoxy or phenyl and —R₅—Y is benzyl optionally substitued by alkyl, alkoxy or phenyl.

In the products of formulae I_D, I_E, I_B, I_G and I and in what follows: the term linear or branched alkyl preferably includes methyl, ethyl, n-propyl, isopropyl, n-butyl, isobutyl, sec-butyl and tert-butyl but can also be pentyl or hexyl and particularly isopentyl and isohexyl. The term linear or branched alkenyl preferably includes vinyl, allyl, 1-propenyl, butenyl and particularly buten-1-yl or pentenyl and the term linear or branched alkynyl preferably means ethynyl, propargyl, butynyl or pentynyl radical.

The term acyl includes decanoyl and dodecanoyl, preferably acetyl, propionyl, butyryl or benzoyl, but it can also be valeryl, hexanoyl, acryloyl, crotonoyl or carbamoyl and formyl. The term esterified carboxy preferably includes optionally substituted lower alkoxy as indicated above such as methoxycarbonyl, ethoxycarbonyl, aminoalkoxycarbonyl such as aminobutoxycarbonyl in which the amino group can be substituted or cyclized to have the values indicated for

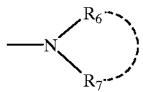

as defined above and hereafter, tert-butoxycarbonyl or benzyloxycarbonyl. The term amidified carboxy preferably includes

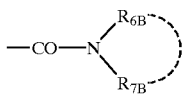

in which R_{6B} and R_{7B} have the meanings indicated above. The term halogen preferably means chlorine, but can also be fluorine, bromine or iodine.

The term cycloalkyl preferably means cyclopropyl, cyclopentyl or cyclohexyl but also cyclobutyl. The term acyloxy means groups wherein the acyl has the meaning indicated above and for example acetoxy and propionyloxy.

The term linear or branched alkoxy preferably is methoxy or ethoxy, but can also be propoxy, isopropoxy, linear, secondary or tertiary butoxy. The term linear or branched alkylthio includes the alkyl being, for example, the values indicated above for alkyl and includes preferably methylthio or ethylthio, but can also be propylthio, isopropylthio, n-butylthio, sec-butylthio, tert-butylthio, isopentylthio or isohexylthio.

The term aryl includes carbocyclic or heterocyclic monocyclic or condensed rings, it being understood that the heterocyclics can contain one or more heteroatoms chosen from oxygen, nitrogen or sulfur and when these heterocyclics contain more than one heteroatom, the heteroatoms of these heterocyclic radicals can be identical or different. The monocyclic preferably contains 5 or 6 links. Examples of carbocyclic monocyclic include phenyl and among the heterocyclic monocyclics are for example thienyl, furyl, pyrannyl, pyrrolyl, imidazolyl, pyrazolyl, pyridyl, pyrazinyl, pyrimidinyl, pyridazinyl, thiazolyl, oxazolyl, furannyl, pyrrolinyl such as delta 2-pyrrolinyl, imidazolinyl such as delta 2-imidazolinyl, pyrazolinyl such as delta 3-pyrazolinyl as well as the position isomers of the heteroatom(s) which they can contain such as tetrazolyl, isothiazolyl or isoxazolyl.

The condensed rings preferably contain 8 to 10 ring members. Among the carbocyclics having condensed rings are for example, naphthyl and phenanthryl. Among the heterocyclics of condensed rings, there can be mentioned, for example, benzothienyl, naphtho [2,3-b]thienyl, indanyl, indenyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also condensed polycyclic systems of heterocyclic monocyclics as defined above, such as furo[2,3-b]pyrrole or thieno[2,3-b]furan. Aryls, include phenyl, naphthyl, thienyl such as thien-2-yl and thien-3-yl, furyl such as fur-2-yl, pyridyl such as pyrid-3-yl, pyrimidyl, pyrrolyl, thiazolyl, isothiazolyl, diazolyl, triazolyl, tetrazolyl, thiadiazolyl, thiatriazolyl, oxazolyl, oxadizolyl, 3- or 4-isoxazolyl. Condensed heterocyclics containing at least one heteroatom chosen from sulfur, nitrogen and oxygen include benzo-thienyl such as benzothien-3-yl, benzofuryl, benzopyrolyl, benzimidazolyl, benzoxazolyl, thionaphthyl, indolyl or purinyl. Such aryls can be optionally substituted such as N-substituted pyrrolyl, for example N-methylpyrrolyl, substituted 3- or 4-isoxazolyl for example 3-aryl-5-methylisoxazol-4-yl, the aryl being for example phenyl or halophenyl.

The term arylalkyl and arylalkenyl which respectively the alkyl, alkenyl and aryl radicals can take the values defined above for these groups. Examples of such arylalkyl include benzyl, diphenylmethyl, triphenylmethyl, naphthylmethyl, indenylmethyl, thienylmethyl such as thien-2-ylmethyl, furylmethyl such as furfuryl, pyridylmethyl, pyrimidylmethyl or pyrrolylmethyl, it being understood that in the non-exhaustive list of examples of groups as mentioned above, the alkyl can also be ethyl, propyl or butyl such as for example in phenethyl. Examples of arylalkenyl include the examples given above for arylalkyl in which the alkyl is replaced by an alkenyl such as phenylvinyl or phenylallyl, it being understood that in these, the phenyl can also be replaced by a naphthyl or pyridyl or also for example one of the aryls as defined above in the non-exhaustive list of aralkyl.

The terms aryloxy and arylthio include those in which the aryl can have the values defined above. In a non-exhaustive fashion, examples of such aryloxy and arylthio include phenoxy, naphthyloxy, pyridyloxy, phenylthio and naphthylthio.

In the products of formulae $I_D$, $I_E$, $I_B$, $I_G$ and I and in what follows: the terms monocyclic and condensed rings designate aryl radicals, that is unsaturated carbocyclic or heterocyclic as defined above, but also include saturated heterocyclics, it being understood that the heterocyclics defined above can contain one or more heteroatoms chosen from oxygen, nitrogen or sulfur and that when these heterocyclics contains more than one heteroatom, the heteroatoms of these heterocyclics can be identical or different. Among the saturated heterocyclic monocyclics pyrrolidinyl, imidazolidinyl, pyrazolidinyl, piperidyl, piperazinyl or morpholinyl. Among the saturated heterocyclics of condensed rings are diaza-1,10-anthryl-4.

The term linear or branched alkylene preferably is the methylene and ethylene but also may be n-propylene, isopropylene, n-butylene, isobutylene, sec-butylene and tert-butylene. The term carbamoyl means non-substituted carbamoyl or substituted carbamoyl for example as indicated hereafter for

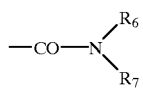

In particular, substituted carbamoyl includes a lower N-monoalkyl carbamoyl such as N-methylcarbamoyl, N-ethylcarbamoyl, a lower N,N-dialkyl carbamoyl such as N,N-dimethylcarbamoyl, N,N-diethylcarbamoyl; an N-(lower hydroxylalkyl) carbamoyl such as N-(hydroxymethyl) carbamoyl, N-(hydroxyethyl) carbamoyl, a lower carbamoylalkyl such as carbamoylmethyl, carbamoylethyl.

The amino radicals which can be represented by one or more of the optional substituents of the products of formulae $I_D$, $I_E$, $I_B$, $I_G$, and I and in what follows can represent or carry in particular

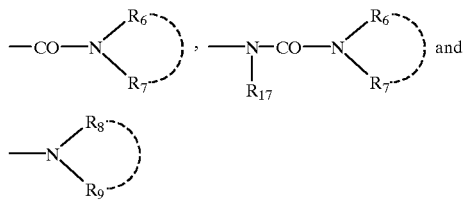

which individually are linked to the nitrogen atom and are chosen from hydrogen alkyl preferably to give monoalkyl- or dialkylamino in which the linear or branched alkyl contain 1 to 6 carbon atoms and particularly methyl, ethyl, isopropyl, trifluoromethyl, pentafluoroethyl, hydroxymethyl, hydroxyethyl, methoxymethyl, methoxyethyl, ethoxymethyl. The alkenyl is as defined above and preferably is vinyl and allyl. The aryl or arylalkyl as defined above, carbocyclic or heterocyclic, and particularly, tetrazolyl, benzyl, phenethyl, naphthyl, indolyl, indolinyl, thienyl, furyl, pyrrolyl, pyridyl, pyrrolidinyl, piperidino, morpholino, piperazinyl, these being optionally substituted by one or more groups as defined above such as methylpiperazinyl, fluoromethylpiperazinyl, ethylpiperazinyl, propylpiperazinyl, phenylpiperazinyl or benzylpiperazinyl.

The above groups represent in a non-exhaustive fashion, —NH-aryl such as —NH-tetrazolyl; —NH-alkyl, —N-(alkyl)$_2$, —NH—CO—NH-alkyl such as —NH—CO—NH-tBu, —NH—CO—NH-n-propyl; —NH—CO—NH-aryl radicals such as —NH—CO—NH-tetrazolyl or —NH—CO—NH-pyridyl or —N(alkyl)-CO—NH-tetrazolyl, it being understood that in all these the alkyl and aryl can have the values indicated above for them and are optionally substituted as indicated above for them.

When $R_6$ and $R_7$ on the one hand or $R_8$ and $R_9$ on the other form a heterocycle with the nitrogen atom to which they are attached, includes pyrrolyl, imidazolyl, pyridyl, pyrazinyl, pyrimidyl, indolyl, indolinyl, purinyl, quinolyl, pyrrolidinyl, piperidyl, piperidino, morpholino, piperazinyl. These can be optionally substituted by the subtituents already mentioned and particularly one or more chosen from chlorine and fluorine, methyl, ethyl, isopropyl, tert-butyl, methoxy, ethoxy, propoxy, benzoyl, methoxycarbonyl, ethoxycarbonyl such as for example in methylpiperazinyl, ethylpiperazinyl, propylpiperazinyl, phenylpiperazinyl or benzylpiperazinyl. In these last two, the phenyl and benzyl can be substituted as indicated previously for aryl, arylalkyl and arylalkenyl.

The acyls represented by $R_8$ and $R_9$ are as defined previously and can be chosen for example from acetyl, propionyl, butyryl, valeryl or carbamoyl.

$Y_1$ and $Y_2$ can have the values defined above for monocyclic aryl or condensed rings, it being understood that in the case where B is a single bond, $Y_2$ can also be non-cyclized such as hydrogen, cyano or free, salified or esterified carboxy. The esterified carboxy preferably is a lower alkoxycarbonyl such as methoxycarbonyl, ethoxycarbonyl or benzyloxycarbonyl.

$Y_1$ or $Y_2$ can individually be aryl optionally substituted by one or more members chosen, preferably, from halogen and

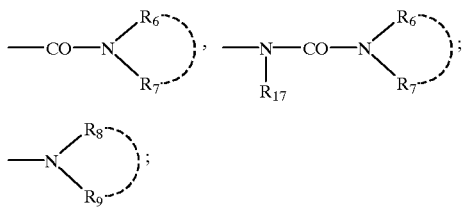

—$(CH_2)_{m1}$—$S(O)_{m2}$—$Z'R'_{14}$, hydroxyl, nitro, tetrazole, isoxazole, alkyl, alkenyl, alkoxy, acyl and free, salified, esterified or amidified carboxy as defined above and hereafter.

The carboxy of the products of formula I can be salified, esterified or amidified by the various groups known to one skilled in the art. Among the salification compounds are mineral bases such as an equivalent of sodium, potassium, lithium, calcium, magnesium or ammonium or organic bases such as methylamine, propylamine, trimethylamine, diethylamine, triethylamine, N,N-dimethylethanolamine, tris-(hydroxymethyl)-amino-methane, ethanolamine, pyridine, picoline, dicyclohexylamine, morpholine benzylamine, procaine, lysine, arginine, histidine, N-methylglucamine.

Among the esterification compounds are alkyls for forming alkoxycarbonyl such as methoxycarbonyl, ethoxycarbonyl, tert-butoxycarbonyl or benzyloxycarbonyl, the alkyls being optionally substituted for example by halogen, hydroxyl, alkoxy, acyl, acyloxy, alkylthio, amino or aryl such as chloromethyl, hydroxypropyl, methoxymethyl, propionyloxymethyl, methylthiomethyl, dimethylaminoethyl, benzyl or phenethyl.

Among the amidification compounds are —$CO_2$—NH—COOH, —$CO_2$—NH—COO aryl, —$CO_2$—NH—COO alkyl, —$CO_2$—NH—$SO_2O$ alkyl, —$CO_2$—NH—$SO_2$—O aryl, —$CO_2$—NH—$SO_2$—$N(alkyl)_2$; in which the alkyl and aryl have the meanings indicated above and are optionally substituted as also indicated above. Notably, aryl is an optionally salified phenyl or tetrazolyl.

The addition salts with mineral or organic acids of the products of formulae $I_D$, $I_E$, $I_B$, $I_G$ and I, can be, for example, the salts formed with hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid and alkylmonsulfonic acids such as methanesulfonic acid, ethanesulfonic acid, propanesulfonic acid, alkyldisulfonic acids such as methanedisulfonic acid, alpha, betaethanedisulfonic acid, arylmonosulfonic acids such as benzensulfonic acid and aryldisulfonic acids.

The carboxy of the products of formulae $I_D$, $I_E$, $I_G$ and I, can be salified by mineral bases such as an equivalent of sodium, potassium, lithium, calcium, magnesium or ammonium or organic bases such as methylamine, propylamine, trimethylamine, diethylamine, triethylamine, N,N-dimethylethanolamine, tris(hydroxymethyl)-amino methane, ethanolamine, pyridine, picoline, dicyclohexylamine, morpholine, benzylamine, procaine, lysine, arginine, histidine, N-methylglucamine.

The alkyl, alkenyl and alkynyl as defined above as well as the alkyl or alkenyl of alkylthio, arylalkyl and arylalkenyl as defined above, can be non-substituted or carry one or more substituents chosen from the group formed by halogen such as chloro or bromo, as in, for example, 2-bromoethyl, hydroxyl, aryl as defined above, either a monocyclic or condensed rings, carbocyclic or heterocyclic, it being understood that the heterocyclics as defined above can contain one or more heteroatoms chosen from oxygen, nitrogen or sulfur and that when these heterocyclics contain more than one heteroatom, the heteroatoms of these heterocyclics can be identical or different. This heterocyclic can be linked by a carbon atom or, if appropriate, by a nitrogen atom; an arylalkyl in which the aryl is as defined above; cycloalkyl, for example, cyclopropyl, cyclopentyl or cyclohexyl, cycloalkenyl such as cyclohexenyl can be optionally substituted, among which there can be mentioned 1,3-dimethyl cyclohexene; an alkoxy as defined above, for example, methoxy, ethoxy, n-propoxy or iso-propoxy for example, methoxymethyl or 1-ethoxyethyl; a substituted alkoxy such as (tri-haloalkyl)-oxy such as, for example, trifluoromethoxy; aryloxy, for example, phenoxy; aralkoxy, for example, benzyloxy, mercapto, alkylthio, for example methylthio or ethylthio, substituted alkylthio such as trihaloalkylthio such as trifluoromethylthio, arylthio, aralkylthio, amino as in 2-aminoethyl; amino substituted by one or more chosen from alkyl, alkenyl, aryl and arylalkyl as defined above such as monalkylamino like methylamino or ethylamino, such as dialkylamino i.e. dimethylamino, nitro, cyano, azido, carboxy, esterified carboxy such as methoxycarbonyl or ethoxycarbonyl; formyl; acyl such as acetyl, propionyl or benzoyl; acyl sustituted by an amino as defined above or by cyclic linked to the acyl radical by a nitrogen, this cyclic being able to optionally contain one or more heteroatoms chosen from nitrogen, oxygen or sulfur and as defined above; acyloxy such as acetoxy or propionyloxy, carbamoyl, substituted carbamoyl such as lower N-monoalkyl carbamoyl, such as N-methylcarbamoyl, N-ethylcarbamoyl, a lower N,N-dialkylcarbamoyl such as N,N-dimethylcarbamoyl, N,N-diethylcarbamoyl, an N-(lower hydroxyalkyl) carbamoyl such as N-(hydroxymethyl) carbamoyl, N-(hydroxyethyl) carbamoyl, a lower carbamoylalkyl such as carbamoylmethyl, carbamoylethyl, phthalimido, acylamido such as acetamido or benzamido, alkoxycarbonylamino such as methoxycarbonylamino or ethoxycarbonylamino, or (arylalkyl) oxycarbonylamino such as benzyloxycarbonylamino.

The aryl and alkyloxy as defined above and the aryl of arylalkyl and arylalkenyl as defined above can be non-substituted or carry one or more substituents chosen from the list indicated above for the optional substituents of alkyl, alkenyl and alkynyl as defined above. Examples include o-chloro-phenyl but can also be substituted by one or more members chosen from the group formed by lower alkyl, for example methyl, ethyl, or also isopropyl or tert-butyl, alkenyl, substituted alkyl such as trihaloalkyl as in trifluoromethyl, alkenyl such as vinyl or allyl, alkynyl such as propargyl.

Preferably the products of formulae $I_D$, $I_E$, $I_B$, $I_G$ and I are characterized in that the individual substituents which can be carried by:

a) alkyl, alkenyl and alkynyl of $R_{1B}$ and $R_1$;
b) alkyl, alkenyl, alkynyl, alkoxy and alkylthio of $R_B$, $R_{1B}$, $R_{2B}$ $R_{3B}$, R, $R_1$, $R_2$ and $R_3$;
c) aryl, arylalkyl, arylalkenyl, aryloxy and arylthio of $R_B$, $R_{1B}$, $R_{2B}$, $R_{3B}$, R, $R_1$, $R_2$ and $R_3$,
d) alkyl, alkenyl and aryl of $R_{14}$ are chosen from the group consisting of halogen, hydroxyl, cyano, nitro, formyl, acyl or acyloxy of up to 6 carbon atoms, benzyl, carboxy free, salified or esterified by alkyl of 1 to 6 carbon atoms, alkyl and alkenyl of up to 6 carbon atoms and optionally substituted by one or more substituents chosen from halogen, hydroxyl, alkoxy of 1 to 6 carbon atoms, carbamoyl, free or esterified carboxy, tertrazole, alkoxy and alkylthio of 1 to 6 carbon atoms, aryl and arylalkyl in which the alkyl contains 1 to 6 carbon atoms, and the aryl and aralkyl are monocyclic of 5 or 6 ring members or condensed rings of 8 to 10 ring members optionally containing one or more heteroatoms chosen from oxygen, nitrogen and sulfur and optionally substituted by one or more radicals chosen from halogen, hydroxyl, cyano, trifluoromethyl, nitro, alkyl, alkenyl, alkoxy and acyl of up to 6 carbon atoms, free, salified or esterified carboxy,

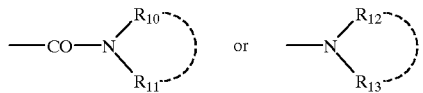

in which:
either $R_{10}$ and $R_{11}$ or $R_{12}$ and $R_{13}$ individually are hydrogen, alkyl or alkenyl of up to 6 carbon atoms and optionally substituted by one or more members chosen from halogen and hydroxyl, alkyl or alkenyl of 2 to 6 carbon atoms substituted by an alkoxy of 1 to 6 carbon atoms, aryl or aralkyl in which the alkyl contains 1 to 6 carbon atoms, and aryl and aralkyl are monocyclic of 5 or 6 ring members or condensed rings of 8 to 10 ring members optionally containing one or more heteroatoms chosen from oxygen, nitrogen and sulfur and being optionally substituted by at least one member chosen from halogen, hydroxyl, cyano, trifluoromethyl, nitro, alkyl, alkenyl, alkoxy and acyl of up to 6 carbon atoms, free, salified or esterified carboxy, or $R_{10}$ and $R_{11}$ or $R_{12}$ and $R_{13}$ form respectively with the nitrogen atom to which they are attached a monocyclic of 5 or 6 ring members or condensed rings of 8 to 10 ring members optionally containing at least one heteroatom chosen from oxygen, nitrogen and sulfur and optionally substituted by at least one member chosen from halogen, hydroxyl, cyano, trifluoromethyl, nitro, alkyl, alkenyl, alkoxy and acyl of up to 6 carbon atoms, free, salified or esterified carboxy, or $R_{12}$ and $R_{13}$ individually or one of $R_{10}$ and $R_{11}$, is acyl of a carboxylic acid of up to 6 carbon atoms, the said products being in all possible racemic, enantiomeric or diastereoisomeric isomer forms, as well as their addition salts with mineral and organic bases of said products.

The

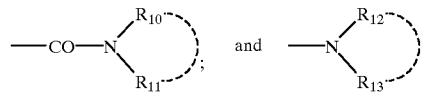

as defined above can have respectively the same values as those defined for

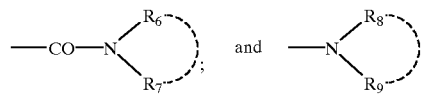

Among the substituents which can be contained by the alkyl, alkenyl, alkynyl, alkoxy, alkylthio, aryl, aralkyl and aralkenyl as defined above are preferbly halogen such as chloro and bromo; hydroxyl; acyl such as acetyl, propionyl, butyryl, valeryl, hexanoyl, acryloyl, crotonoyl or carbamoyl, benzoyl, esterified carboxy preferably a lower alkoxy carbonyl such as methoxycarbonyl, ethoxycarbonyl or benzyloxycarbonyl; alkyl such as methyl or ethyl; amino, substituted amino such as monoalkyl- and dialkylamino like methylamino, ethylamino or dimethylamino; alkoxy such as methoxy, ethoxy or isopropoxy; aryl such as phenyl, biphenyl, naphthyl, indenyl, indolyl or indolinyl; aralkyl such as benzyl or phenethyl; alkyl, alkoxy and aryl as defined above themselves substituted by at least one members of the group formed of hydroxyl, alkyl and alkoxy such as methyl, ethyl, tert-butyl, methoxy, ethoxy, isopropoxy; substituted amino such as monoalkyl- and dialkylamino, for example, methylamino, ethylamino or dimethylamino; carbocyclic or heterocyclic monocyclics of up to 6 ring members such as phenyl, pyrannyl, pyridyl, pyrimidinyl, pyridazinyl, pyrazinyl, piperidyl, piperazinyl, piperidino and morpholino; carbocyclic or heterocyclic monocycles of 5 ring members such as furyl, pyrrolyl, pyrrolinyl, imidazolyl, or pyrazolyl, isothiazolyl, isoxazolyl, pyrrolidinyl, imidazolidinyl, pyrazolidinyl; carbocyclic or heterocyclic condensed rings such as naphthyl, indolyl, quinolyl or purinyl as well as their position isomers of heteroatom(s), for example nitrogen such as indazolyl or isoquinolyl.

When such heterocycles contain one or more nitrogen atoms, the nitrogen atoms may be substituted such as by alkyl or alkoxy of 1 to 5 carbon atoms, as defined above, methyl, ethyl, isopropyl, tert-butyl, methoxy or ethoxy, phenyl or benzyl optionally substituted by the substituents already mentioned above for the aryl and arylalkyl. Examples includes methylpiperazinyl, ethylpiperazinyl, propylpiperazinyl, phenylpiperazinyl or benzylpiperazinyl.

Among the particularly preferred are phenyl, naphthyl, pyridyl, piperazinyl, pyrimidinyl, pyrazinyl and pyrazinyl.

Such products of formula $I_B$ and I can therefore be quinoline derivatives when A is C—$R_4$ as defined above and cinnoline derivatives when A is nitrogen.

A particular subject of the invention are the products of the formula

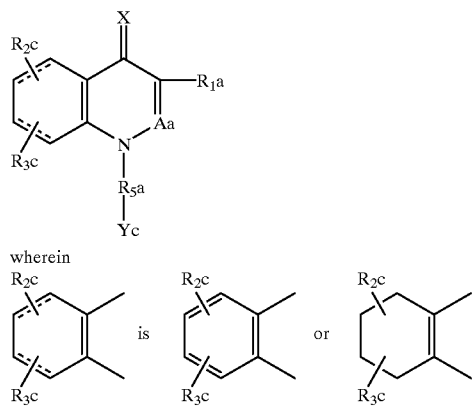

wherein

R2c/R3c is and $R_{1a}$ is methyl, ethyl, n-propyl, n-propenyl, n-butyl or butenyl, $R_{2c}$ and $R_{3c}$ individually are chosen from the group consisting of hydrogen, halogen, hydroxyl, mercapto, cyano, nitro, formyl, benzoyl, acyl of up to 6 carbon atoms, sulfo, carboxy radicals free, salified or esterified by alkyl of 1 to 4 carbon atoms, tetrazole, alkyl, alkenyl, alkoxy and alkylthio of up to 6 carbon atoms, phenyl, naphthyl, benzyl and phenylthio optionally substituted by at least one member of the group consisting of halogen, hydroxyl, alkoxy of 1 to 4 carbon atoms, trifluoromethyl, cyano, free, salified or esterified carboxy, tetrazole, isoxazole, pyrrolidinyl, pyrrolidinylcarbonyl and phenyl optionally substituted by at least one member of the group consisting of halogen, hydroxyl, alkyl and alkoxy of 1 to 4 carbon atoms, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, pyrrolidinylcarbonyl, piperazinylcarbonyl, all the piperazinyls being optionally substituted on the second nitrogen atom by alkyl or phenyl optionally substituted by at least one member of the group consisting of hydroxyl, halogen, nitro, alkyl or alkoxy of 1 to 4 carbon atoms, trifluoromethyl, cyano, free, salified or esterified carboxy, tetrazole and isoxazole, $A_a$ is nitrogen or C—$R_{4a}$, $R_{4a}$, is hydrogen; acyl of 1 to 6 carbon atoms; cyano, carboxy free, salified or esterified alkyl of 1 to 4 carbon atoms; alkyl of 1 to 6 carbon atoms optionally substituted by at least one member chosen from hydroxyl and halogen, X is oxygen or sulfur, $R_5$ is divalent alkylene of 1 to 4 carbon atoms, $Y_c$ is phenyl or biphenyl optionally substituted by at least one member chosen from the group consisting of hydroxyl, halogen, alkyl and alkoxy of 1 to 4 carbon atoms, trifluoromethyl, cyano, nitro, free, salified or esterified carboxy, tetrazole, isoxazole, —$(CH_2)_p$—$SO_2$—$Z_c$—$R_{14c}$ P is 0 or 1, $Z_c$ is —NH—, —NH—CO—, —NH—CO—NH— or a single bond and $R_{14c}$ is one of the following: methyl, ethyl, propyl, vinyl, allyl, pyridyl, phenyl, benzyl, pyridylmethyl, pyridylethyl, nitropyridyl, pyrimidyl, tetrazolyl, diazolyl, piperidinyl, alkylpiperidinyl, thiazolyl, alkylthiazolyl, tetrahydrofuranyl, methyltetrahydrofuranyl, amino or carbamoyl optionally substituted by one or two members chosen from —$(CH_2)_p$—$SO_2$—$Z_c$—$R_{14c}$ as defined above and alkyl and alkenyl of up to 4 carbon atoms and optionally substituted by at least one member of the group consisting of halogen, hydroxyl, alkyl, alkenyl and alkoxy of up to 4 carbon atoms, trifluoromethyl, cyano, free, salified or esterified carboxy or tetrazolyl; the said products of formula I, being in all possible racemic, enantiomeric and diastereoisomeric isomer forms, as well as the addition salts with mineral and organic acids or with mineral and organic bases of said products of formula $I_c$.

The —$(CH_2)_{m1}$—$S(O)_{m2}$—Z'—$R'_{14}$ may be a compound in which $(CH_2)_{m1}$ is alkylene such as methylene, ethylene, n-propylene or n-butylene and $R'_{14}$ is alkyl or alkenyl chosen from the values defined above or aryl also chosen from the values indicated above such as phenyl, pyridyl, biphenyl, naphthyl, tetrazolyl; the alkyl or alkenyl of $R'_{14}$ can optionally be substituted by aryl chosen from the values defined above to form an aralkyl or aralkenyl radical. These alkyl, alkenyl, aryl, aralkyl and arylalkenyl can be substituted as indicated above.

The following examples are mentioned in a non-exhaustive manner: —$CH_2$—$SO_2$—$NH_2$, —$CH_2$—$SO_2$—NH—$C_6H_5$, $SO_2$—NH—CO—NH—$CH_3$—, —$SO_2$—NH—CO—NH—$C_6H_5$, —$SO_2$—NH—CO—NH—$CF_3$, $SO_2NH$—CO—NH-alkyl, —$SO_2$—NH—CO—NH-tBu, —$SO_2$—NH—CO—NH—$CH_2$—$C_6H_5$, —$SO_2$—NH—CO—NH—$C_6H_4$—Cl $SO_2$—NH—CO—NH-aryl, $SO_2$—NH—CO—NH-tetrazolyl,

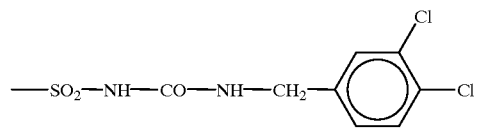

—$SO_2$—NH—CO—NH—CH=CH—$CH_3$,

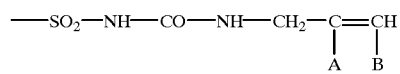

in which A and B are individually chosen from hydrogen, phenyl, pyridyl and pyrimidyl;

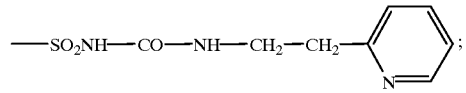

—$SO_2$—NH-tetrazolyl,

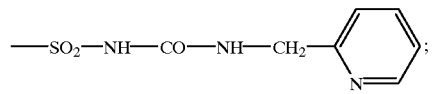

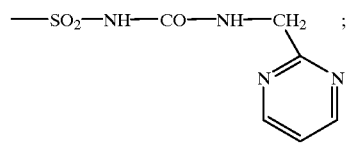

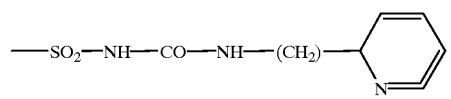

—$SO_2$—NH—$SO_2$-tetrazolyl;
—$SO_2$—NH—$SO_2$—$NH_2$; —$SO_2$—NH—$SO_2$—NH(tBu);
—$SO_2$—NH—$SO_2$-tBu;

and also —NH-(alkyl), —NH-aryl, —NH-tetrazolyl, —SO$_2$—NH—CO$_2$-alkyl,
—SO$_2$—NH—CO$_2$aryl, —SO—$_2$—NH—CO$_2$-tetrazolyl, —NH—CO—NH-aryl,
—NH—CO—NH-tetrazolyl, —CO$_2$—NH—CO$_2$-aryl, —CO$_2$—NH—CO$_2$-tetrazolyl,
—CO$_2$NH—SO$_2$—O-aryl, —CO$_2$NH—SO$_2$—N(alk)$_2$, CO$_2$—NH—SO$_2$—NH$_2$ The aryl of Y$_1$ can be substituted by at least one member chosen from the values of R$_2$ and R$_3$ and especially by —NH—(CH$_2$)$_m$—SO$_2$—Z—R$_{14}$ and —CO—NH(CH$_2$)$_m$—SO$_2$—Z—R$_{14}$ in which the (CH$_2$)$_m$—SO$_2$—Z—R$_{14}$ can take the values indicated above.

For example, the following groups are mentioned in a non-exhaustive manner:
—NH—SO$_2$—CH$_3$, —NH—SO$_2$—C$_6$H$_5$, —NH—SO$_2$—CF$_3$,
—NH—CH$_2$—SO$_2$—NH—C$_6$H$_5$, —CO—NH—SO$_2$—C$_2$H$_5$, —CO—NH—SO$_2$—CH$_3$,
—CO—NH—SO$_2$—CH$_2$—C$_6$H$_5$.

A quite particular subject of the invention is the products of formula I$_B$, I and I$_c$ as defined above, and corresponding to the formula

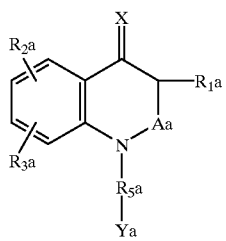

I$_a$

R$_{1a}$ is methyl, ethyl, n-propyl, n-propenyl, n-butyl or butenyl, R$_{2a}$ and R$_{3a}$ are individually chosen from the group consisting of hydrogen, halogen, hydroxyl, mercapto, cyano, nitro, formyl, benzoyl, acyl of 1 to 6 carbon atoms, sulfo, carboxy free, salified or esterified by alkyl of 1 to 4 carbon atoms, tetrazolyl, alkyl, alkoxy and alkythio of 1 to 6 carbon atoms, phenyl, naphthyl, benzyl and phenylthio optionally substituted by at least one member of the group consisting of halogen, hydroxyl, alkoxy of 1 to 4 carbon atoms, trifluoromethyl, cyano, free, salified or esterified carboxy, tetrazolyl and isoxazolyl, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, piperazinylcarbonyl, all the piperazinyl being optionally substituted on the second nitrogen atom by alkyl or phenyl optionally substituted by one or more members chosen from hydroxyl, halogen, nitro, alkyl or alkoxy of 1 to 4 carbon atoms, trifluoromethyl, cyano, free, salified or esterified carboxy, tetrazole and isoxazole, A$_a$ is nitrogen or C—R$_{4a}$, R$_{4a}$ is hydrogen, acyl of 1 to 6 carbon atoms, cyano, carboxy free, salified or esterified by alkyl of 1 to 4 carbon atoms or alkyl of 1 to 6 carbon atom optionally substituted by one or more members chosen from hydroxyl and halogen, X is oxygen or sulfur, R$_5$ is divalent alkylene of 1 to 4 carbon atoms, Y$_a$ is phenyl or biphenyl optionally substituted by at least one member chosen from hydroxyl, halogen, alkyl and alkoxy of 1 to 4 carbon atoms, trifluoromethyl, cyano, nitro, free, salified or esterified carboxy, tetrazole and isoxazole, the said products of formula I$_a$ being in all possible racemic, enantiomeric and diastereoisomeric isomer forms, as well as the addition salts with mineral and organic acids or with mineral and organic bases of said products of formula I$_a$.

Among the preferred compounds of formula I$_D$ are those wherein D$_1$, D$_2$ and at least one of D$_3$ and D$_4$ is methine or methylene optionally substituted by one of R$_B$, R$_{2B}$ and R$_{3B}$, R$_1$ is methyl, ethyl, n-propyl, n-propenyl, n-butyl, cyclopropyl, free or esterified carboxy, R$_B$, R$_{2B}$ and R$_{3B}$ are individually chosen from the group of: hydrogen, halogen, mercapto, and alkylthio, alkyl and alkenyl of up to 6 carbon atoms optionally substituted by at least one member of the group consisting of halogen, hydroxyl, alkoxy of 1 to 4 carbon atoms, alkylthio, phenylthio, pyridylthio in which the alkyl contains 1 to 4 carbons and the sulfur atom is optionally oxidized in the form of sulfoxide or sulfone, amino, mono- and dialkylamino, pyrrolidinyl, morpholinyl, piperidinyl, phenyl, carboxy free, salified or esterified by alkyl of 1 to 4 carbon atoms optionally substituted as indicated above, phenyl, pyridyl, pyrrolidinyl, pyrrolidinyl-carbonyl, morpholinyl-carbonyl, carbamoyl, dialkylcarbamoyl, piperidynyl-carbonyl, A is nitrogen or CH optionally substituted by a free or esterified carboxy, X is oxygen or sulfur, R$_5$ is methylene, Y is phenyl or biphenyl optionally substituted by at least one member chosen from cyano, free, salified or esterified carboxy, tetrazolyl, and isoxazolyl.

Preferred of formulae I$_D$, I$_B$, I$_B$, I$_G$ and I are those wherein: R$_B$ or R$_1$ is methyl, ethyl, n-propyl, n-propenyl, n-butyl, R$_{2B}$ or R$_{3B}$ or R$_2$ and R$_3$ are individually chosen from the group consisting of hydrogen, mercapto and alkylthio and alkyl of 1 to 6 carbon atoms optionally substituted by at least one member of the group consisting of halogen, hydroxyl, amino, mono- and dialkylamino, pyrrolidinyl, morpholinyl, piperidinyl, carboxy, free, salified or esterified by alkyl of 1 to 4 carbon atoms, pyrrolidinyl-carbonyl, morpholinyl-carbonyl, carbamoyl, dialkyl-carbamoy, piperidynyl-carbonyl, A is nitrogen or CH, X is oxygen or sulfur, R$_5$ is methylene, Y$_B$ or Y is phenyl or biphenyl optionally substituted by one or more members chosen from cyano, free, salified and esterified carboxy, tetrazolyl and isoxazolyl.

Specific preferred compounds of the invention are
4'-[(3-butyl-1,4-dihydro-4-oxo-1-quinolinyl)-methyl]-(1,1'-biphenyl)-2-carboxylic acid,
4'-[(3-butyl-1,4-dihydro-4-thioxo-1-quinolinyl)-methyl]-(1,1'-biphenyl)-2-carboxylic acid,
3-butyl-1-[(2'-carboxy-(1,1'-biphenyl)-4-yl)-methyl]-1,4-dihydro-4-oxo-7-quinolinecarboxylic acid,
4'-[(3-butyl-1,4-dihydro-8-bromo-4-oxo-1-quinolinyl)-methyl]-(1,1'-biphenyl)-2-carboxylic acid,
4'-[(3-butyl-1,4-dihydro-7-(hydroxymethyl)-4-oxo-1-quinolinyl)-methyl]-(1,1'-biphenyl)-2-carboxylic acid,
4'-[(3-butyl-1,4-dihydro-4-oxo-7-[(1-pyrrolidinyl)-carbonyl]-1-quinolinyl)-methyl]-(1,1'-biphenyl)-2-carboxylic acid,
4'-[(3-butyl-1,4,5,6,7,8-hexahydro-4-oxo-1-[(1-quinolinyl)-methyl]-( 1,1'-biphenyl)-2-carboxylic acid,
4'-[(3-butyl-1,4,5,6,7,8-hexahydro-6-methyl-4-oxo-1-quinolinyl)-methyl]-(1,1'-biphenyl)-2-carboxylic acid,
3-butyl-1,4-dihydro-1-[[2'-(1H-tetrazol-5-yl)-(1,1-biphenyl)-4-yl]-methyl]-8-quinolinecarboxylic acid,
1,4-dihydro-3-methyl-4-oxo-1-[[2'-(1H-tetrazol-5-yl)-(1,1-biphenyl)-4-yl]-methyl]-8-quinolinecarboxylic acid, and
1,4-dihydro-3-ethyl-4-oxo-1-[[2'-(1H-tetrazol-5-yl)-(1,1'-biphenyl)-4-yl]-methyl]-8-quinolinecarboxylic acid.

The process of the invention for the preparation of compounds of formula I$_D$ comprises either reacting a compound of the formula

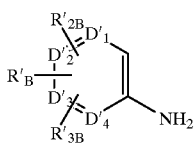

II$_D$ wherein D'$_1$, D'$_2$, D'$_3$, D'$_4$, R'$_B$, R'$_{2B}$ and R'$_{3B}$ have the above definitions respectively for D$_1$, D$_2$, D$_3$, D$_4$, R$_B$, R$_{2B}$ and R$_{3B}$ in which the optional reactive functions are optionally protected by protective groups with a compound of the formula

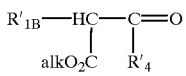

III wherein R$_{1B}$ and R'$_4$ have the above definitions respectively for R$_{1B}$ and R$_4$ in which the optional reactive functions are optionally protected by protective groups and alk is alkyl of 1 to 6 carbon atoms to obtain a compound of the formula

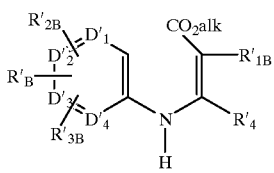

IV$_{D'}$ wherein D'$_1$, D'$_2$, D'$_3$, D'$_4$, R'$_B$, R'$_{1B}$, R'$_{2B}$, R'$_{3B}$, R'$_4$ and alk have the above definitions, cyclizing the latter to obtain a compound of the formula

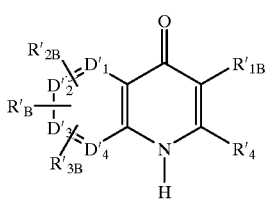

V$_{D'}$ in which D'$_1$, D'$_2$, D'$_3$, D'$_4$, R'$_B$, R'$_{1B}$, R'$_{2B}$, R'$_{3B}$ and R'$_4$ have the meanings indicated above or a product of the formula

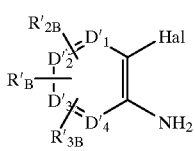

VI$_D$ in which D'$_1$, D'$_2$, D'$_3$, D'$_4$, R'$_B$, R'$_{1B}$, R'$_{2B}$ and R'$_{3B}$ have the above meanings and Hal is halogen, reacting the latter with a product of the formula

VII$_D$ in which R'$_{1B}$ has the above definition to obtain a compound of the formula

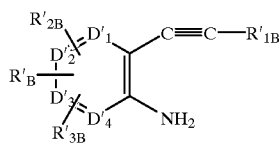

VIII$_D$ in which D'$_1$, D'$_2$, D'$_3$, D'$_4$, R'$_B$, R'$_{1B}$, R'$_{2B}$ and R'$_{3B}$ have the above definitions, subjecting the latter to a cyclization reaction to obtain a compound of the formula

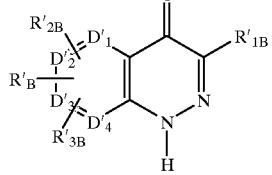

IX$_D$ in which D'$_1$, D'$_2$, D'$_3$, D'$_4$, R'$_B$, R'$_{1B}$, R'$_{2B}$, and R'$_{3B}$ have the meanings above, which products of formulae V$_D$ and IX$_D$ are optionally subjected to a hydrogenation reaction to obtain respectively the products of the formula

V$_{BD}$

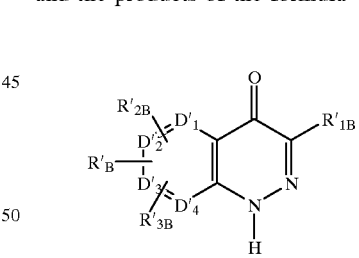

and the products of the formula

IX$_{BD}$ wherein D'$_1$, D'$_2$, D'$_3$, D'$_4$, R'$_B$, R'$_{1B}$, R'$_{2B}$, R'$_{3B}$ and R'$_4$ have the meanings above, and the products of formulae V$_D$, V$_{BD}$, IX$_D$ and IX$_{BD}$ are optionally subjected to a conversion reaction of the oxo into a thioxo and which are reacted with a compound of the formula Hal-R'$_5$—Y'$_B$     X in which Hal is halogen and R'$_5$ and Y'$_B$ have the meanings above, respectively for R$_5$ and Y$_B$ in which the optional reactive functions are optionally protected by protective groups to obtain a product of the formula

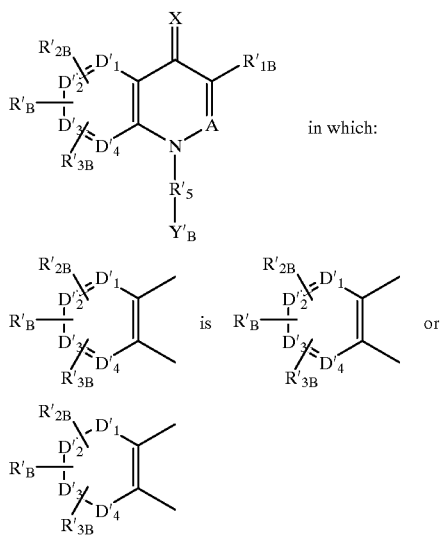

I'$_D$ in which:

is       or $D'_1$, $D'_2$, $D'_3$, $D'_4$, $R'_B$, $R'_{1B}$, $R'_{2B}$, $R'_{3B}$, $R'_4$, $R'_5$ and $Y'_B$ have the meaning above, A is C—$R'_4$ or nitrogen, and X has the meaning indicated above and the products of formula I'$_D$ in which

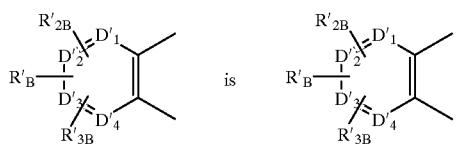

is can optionally be subjected to a hydrogenation reaction to obtain a product of the formula I'$_D$ in which

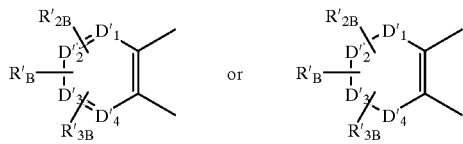

or which product of formula I'$_D$ is optionally subjected to one or more of the following reactions in any order:
a conversion reaction of the C═O oxo function into a C═S thioxo function,
an elimination reaction of the protective groups which can be carried by the protected reactive functions,
a salification reaction by a mineral or organic acid or by a mineral or organic base to obtain the corresponding salt,
an esterification reaction of the acid function,
a saponificatin reaction of the ester function into an acid function,
a conversion reaction of the alkoxy function into a hydroxyl function,
a conversion reaction of the cyano function into an acid function,
a reduction reaction of the carboxy function into an alcohol function,
a resolution reaction of the racemic forms,
the said products of formula I$_D$ thus obtained being in all possible racemic, enantiomeric and diastereoisomeric isomer forms.

The process for the preparation of a compound of formula I$_B$ comprises reacting either a product of the formula

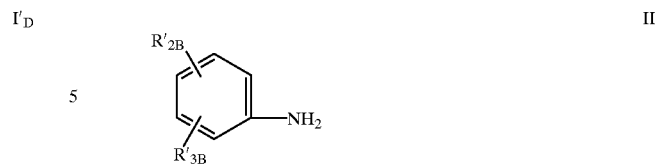

II in which R'$_{2B}$ and R'$_{3B}$ have the meanings above, respectively for R$_B$ and R$_{3B}$ in which the optional reactive functions are optionally protected by protective groups with a product of the formula

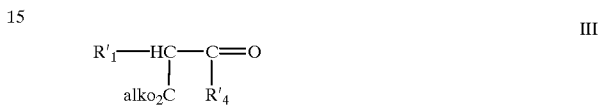

III in which R'$_1$ and R'$_4$ have the meanings above, respectively for R$_1$ and R'$_4$ in which the optional reactive functions are optionally protected by protective groups and alk is alkyl of 1 to 6 carbon atoms to obtain a compound of the formula

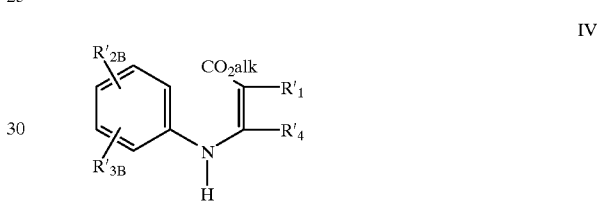

IV in which R'$_1$, R'$_{2B}$, R'$_{3B}$, R'$_4$ and alk have the meanings above, cyclizing the latter to obtain a compound of the formula

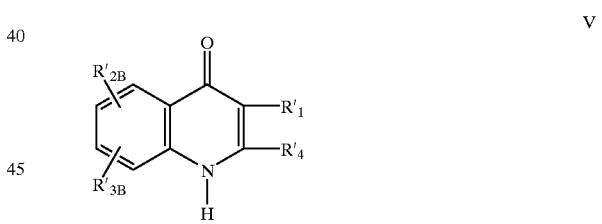

V in which R'$_1$, R'$_{2B}$, R'$_{3B}$ and R'$_4$ have the meanings above or reacting a product of the formula

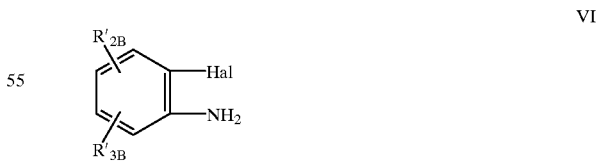

VI in which R'$_{2B}$ and R'$_{3B}$ have the meanings above with a product of the formula

VII

R'$_1$—C≡CH in which R'$_1$ has the meaning indicated above to obtain a compound of the formula

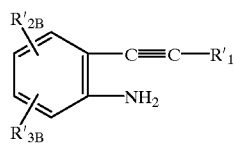

VIII in which Hal is halogen and R'$_1$, R'$_{2B}$ and R'$_{3B}$ have the meanings above, subjecting the latter to a cyclization reaction to obtain a product of the formula

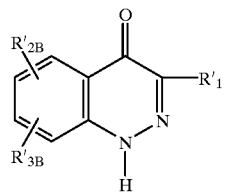

IX in which R'$_1$, R'$_{2B}$ and R'$_{3B}$ have the meanings above, the products of formulae V and IX are optionally subjected to a hydrogenation reaction to obtain respectively the products of the formula

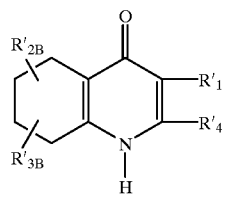

V$_B$ and the products of the formula

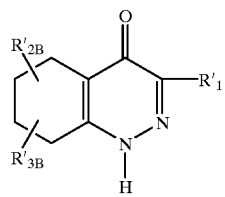

IX$_B$ the products of formulae V, V$_B$, IX, IX$_B$ are optionally subjected to a conversion reaction of the oxo into thioxo and which are reacted with a compound of the formula

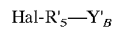

X in which Hal is halogen and R'$_5$ and Y'$_B$ have the meanings above, respectively for R$_5$ and Y$_B$ in which the optional reactive functions are optionally protected by protective groups to obtain a product of the formula

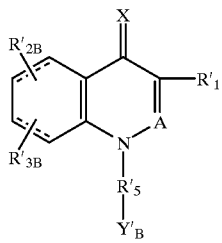

I'$_B$ in which

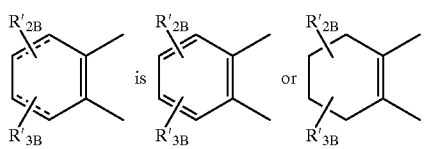

R'$_1$, R'$_{2B}$, R'$_{3B}$, R'$_5$ and Y'$_B$ have the meanings above, A is —C—R'$_4$, R'$_4$ has the previous definition or nitrogen and X has the meaning above, in which products of formula I'$_B$

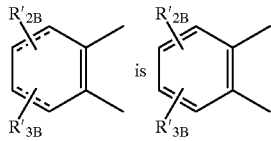

and optionally subjecting the latter to a hydrogenation reaction to obtain a compound of formula I'$_B$ in which

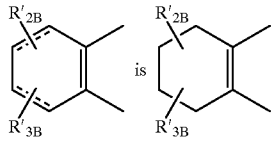

which product of formula I'$_B$ is optionally subjected to one or more of the following reactions in any order:
a conversion reaction of the C=O oxo function into a C=S thioxo function,
an elimination reaction of the protective groups which can be carried by the protected reactive functions,
a salification reaction by a mineral or organic acid or by a mineral or organic base to obtain the corresponding salt,
an esterification reaction of the acid,
a saponification reaction of the ester function into an acid function,
a conversion reaction of the alkoxy function into a hydroxyl function,
a reduction reaction of the carboxy function into an alcohol function,
a resolution reaction of the racemic forms,
the said products of formula I$_B$ obtained being in all possible racemic, enantiomeric and diastereoisomeric isomer forms.

Under the preferred conditions for the process of the invention for the preparation of the products of formula I$_B$, the product of formula IV is obtained by reacting the carbonyl derivative of formula III on the free amine function of the product of formula II in the presence of a solvent such as toluene or an alcohol such as ethanol or also acetic acid at reflux. The reaction can be carried out in the absence of a solvent by taking the mixture to the melting point of the compounds in the optional presence of a desiccating agent such as Siliporite$_R$.

The cyclization reaction of the product of formula IV into the product of formula V can be carried out by heating the compound to its melting point or also in a solvent such as biphenyl oxide or a mixture of phenyl and biphenyl oxide at a temperature of approximately 100° C. to 250° C.

The product of formula VIII can be obtained by reacting the product of formula VII with the halogen derivative of formula VI in the presence of a copper salt such as copper iodide and a catalyst such as a palladium catalyst.

The cyclization reaction of the product of formula VIII into the product of formula IX can be carried out by the action of nitrous acid obtained in situ in the presence of sodium or potassium nitrite in an acid medium such as in hydrochloric acid.

The hydrogenatin reaction of the products of formula VI into the products of formula $V_B$ or of the product of formula IX into the products of formula $IX_B$ can be carried out under the usual conditions known to one skilled in the art and for example in a solvent such as methanol, ethanol, ethyl acetate, acetic acid and by hydrogenation in the presence of platinum oxide, palladium on charcoal or rhodium on charcoal.

The products of formulae V, $V_B$, IX and $IX_B$ can be subjected to a conversion reaction of the oxo function into a thioxo function which can be carried out according to the usual methods known to one skilled in the art such as using the Lawesson reagent or also phosphorous pentasulfide at reflux in a sovlent such as toluene or an alcohol such as ethanol.

The addition of the compound of formula X onto the free amine function of the product of formulae V, $V_B$, IX or $IX_B$ to obtain the products of formula $I'_B$ can be carried out in the presence of a weak base such as sodium or potassium carbonate or also in the presence of sodium hydride at reflux in a solvent such as acetone, ether or also tetrahydrofuran.

The oxo function of the products of formulae V, $V_B$, IX and $IX_B$ can be also protected and the addition reaction therefore operates on the free amine function defined above by simple heating with the product of formula X.

The addition of the compound of formula X onto the free amine function of the product of formula V gives products of formula $I'_B$ in which A is =C—$R'_4$ as defined above and the addition of the product of formula X onto the free amine function of the product of formula IX gives products of formula $I'_B$ in which A is nitrogen.

The product of formula X can also be reacted with the non-protected oxo function of the products of formulae V, $V_B$, IX and $IX_B$ to give the products of the formula

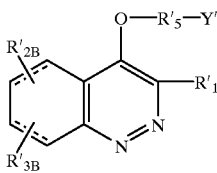

A

In this case, a mixture of products of formulae $I'_B$ and A are obtained by reacting the products of formulae V, $V_B$, IX and $IX_B$ with the compound of formula X under the condition defined above.

The hydrogenation reaction of the products of formula $I_B$ to obtain the other products of formula $I'_B$ can be carried out under the same conditions as those indicated above for the hydrogenation of products of formulae V and IX respectively into products of formulae $V_B$ and $IX_B$.

According to the values of $R'_1$, $R'_{2B}$, $R'_{3B}$, $R'_5$, A, Y' and X, the products of formula $I'_B$ thus obtained constitute or do not constitute the products of formula $I_B$. The products of formula $I'_B$ thus obtained, in particular to give products of formula $I_B$, can be optionally subjected, to one or more of reactions indicated above.

Among these, the conversion reaction of the oxo function into the thioxo function can be carried out as indicated above. The various reactive functions which can be carried by certain reaction compounds defined above can, if necessary, be protected. For example, the hydroxyl, acyl, free carboxy radicals or also the amino and monoalkylamino radicals can be protected by appropriate protective groups.

The following non-exhaustive list of examples of protection of the reactive functions can be mentioned: the hydroxyl groups can be protected by alkyl such as tert-butyl, trialkylsilyl, dihydropyrane, methoxymethyl or tetrahydropyrannyl, the amino groups can be protected by acetyl, trityl, benzyl, tert-butoxycarbonyl, phthalimido or other groups known in the chemistry of peptide, the acyl groups such as the formyl group can be protected in the form of cyclic or non-cyclic ketal such as dimethyl- or diethylketal or ethylene dioxyketal. The acid functions of the products can be if desired, amidified by a primary or secondary amine in methylene chloride in the presence of 1-ethyl-3-(dimethylaminopropyl) carbodiimide hydrochloride at ambient temperature and the acid functions can be protected in the form of esters formed with easily cleavable esters such as benzyl or tert-butyl esters or esters known in the chemistry of peptides.

The elimination of these protective groups is carried out by the usual conditions known to one skilled in the art, notably acid hydrolysis carried out with an acid such as hydrochloric acid, benzene sulfonic acid or p-toluene sulfonic acid, formic acid or trifluoroacetic acid. The phthalimido group is eliminated by hydrazine. A list of different usable protective groups will be found for example in U.S. Pat. No. 5,243,043.

The products described above can also be subjected to salification reactions with a mineral or organic acid or by a mineral or organic base, particularly on the optional carboxy functions, these reactions being able to carried out according to the usual methods known to one skilled in the art. The products described above can also be subjected to esterification reactions on the optional carboxy functions, which can be carried out according the the usual methods known to one skilled in the art.

The optional ester functions of the products can be saponified into an acid function by saponification reactions under the usual conditions known to one skilled in the art, notably by acid or alkaline hydroxysis by sodium hydroxide or potassium hydroxide in an alcoholic medium such as in methanol or also by hydrochloric or sulfuric acid.

The optional alkoxy functions such as methoxy of the products can be converted into a hydroxyl function under the usual conditions known to one skilled in the art by boron tribromide in a solvent such as methylene chloride, by pyridine hydrobromide or hydrochloride or also by hydrobromic acid or hydrochloric acid in water or acetic acid at reflux.

The optional cyano functions of the products can be converted into an acid function under the usual conditions known to one skilled in the art by double hydrolysis carried out in an acid medium such as in a sulfuric acid, glacial acetic acid and water mixture, these three compounds being preferably in equal proportions, or also in a sodium hydroxide-ethanol and water mixture at reflux.

The optional carboxy or esterified carboxy functions of the products can be reduced into an alcohol function by methods known to one skilled in the art and notably by lithium aluminium hydride in a solvent such as tetrahydrofuran or also dioxane or ethyl ether.

The optional optically active forms of the products of formula $I_B$ can be prepared by resolving the racemates by the usual methods.

Also a subject of the invention is a preparation process for the products of formula $I_B$ characterized in that the products of formulae V, $V_B$, IX and $IX_B$ are taken as starting products and the operation takes place as indicated previously.

Also a subject of the invention is a preparation process for the products of formulae V, $V_B$, IX and $IX_B$ characterized in that the products of formula II are taken as starting products and the operation takes place as indicated previously.

The preparation of the products of formula $I_D$ can be carried out under the same conditions as those described above for the preparation of the products of formula $I_B$ by replacing the compounds of formulae II, IV, V, VI, VIII, IX, $V_B$ $IX_B$ and $I'_B$ respectively with the compounds of formulae $II_D$, $IV_D$, $V_D$, $VIII_D$, $IX_D$, $V_{BD}$, $IX_{BD}$ and $I'_D$ whose meanings are respectively indicated above.

Similarly, the process for the preparation of products of formula $I_{EB}$, corresponding to the products of formula $I_B$, as defined above, in which A is —C—$R_{4E}$ and $R_{4E}$ s hydrogen or an optionally esterified carboxy comprises reacting either a product of the formula

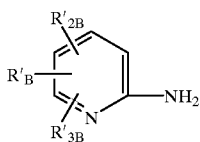

$II_E$ in which $R'_B$, $R'_{2B}$ and $R'_{3B}$ have the meanings above, respectively for $R_B$, $R_{2B}$ and $R_{3B}$ in which the optional reactive functions are optionally protected by protective groups with a product of the formula

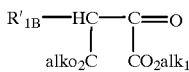

XI in which $R'_{1B}$ has the meaning above for $R_{1B}$ in which the optional reactive functions are optionally protected by protective groups and alk and alk, are individually alkyl of 1 to 6 carbon atoms, to obtain a compound of the formula

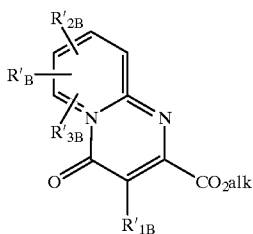

XII in which $R'_B$, $R'_{1B}$, $R'_{2B}$, $R'_{3B}$ and alk have the meanings above or a compound of the formula

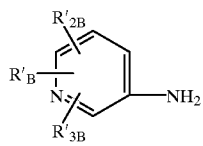

$II_F$ in which $R'_B$, $R'_{2B}$ and $R'_{3B}$ have the meanings above, with a product of formula XI as defined above, to obtain a compound of the formula

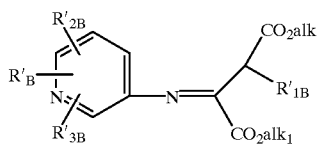

XIII in which $R'_B$, $R'_{1B}$, $R'_{2B}$, $R'_3B$, alk and $alk_1$ have the meanings above, the products of formulae XII and XIII converting into a compound of the formula

XIV in which $R'_B$, $R'_{1B}$, $R'_{2B}$, $R'_{3B}$ and $alk_1$ have the meanings above and $D_5$ and $D_6$ have the meanings above, which products are optionally subjected jected to a hydrogenation reaction to obtain a compound of the formula

XV in which $D_5$, $D_6$, $R'_B$, $R'_{1B}$, $R'_{2B}$, and $R'_{3B\ and\ alk1}$ have the meanings above, which products of formula XIV and XV are optionally subjected to a saponification reaction, then to a decarboxylation reaction to obtain the corresponding products of the formula

XIV'

-continued

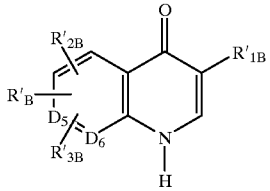

and formula

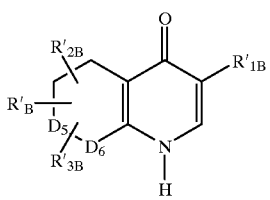

the products of formulae XIV, XIV', XV and XV' are optionally subjected to a conversion reaction of the oxo function to a thioxo function and reacted with a compound of the formula Hal-R'$_5$—Y'$_B$   X in which R'$_5$ and Y'$_B$ have the meanings above for R$_5$ and Y respectively in which the optional reactive functions are optionally protected by protective groups to obtain a product of the formula

I'$_{EB}$

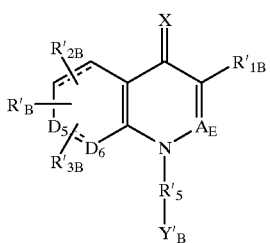

in which:

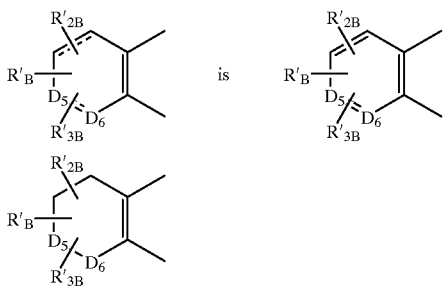

D$_5$, D$_6$, R'$_B$, R'$_{2B}$, R'$_{3B}$, R'$_5$ and Y'$_B$ have the meanings above, A$_B$ is —C—R$_{4E}$ in which R$_{4E}$ is hydrogen or an optional esterified carboxy and X has the meaning above to obtain a product of the formula I'$_{EB}$ where

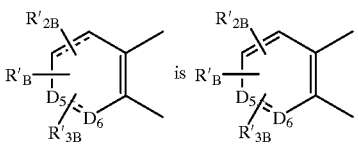

which optionally can be subjected to a hydrogenation reaction to obtain the products of formula I'$_{EB}$ in which

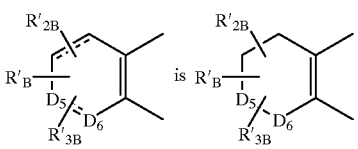

which products of formula I'$_{EB}$ is subjected optionally to one or more of the following reactions in any order:
a conversion reaction of the C=O oxo function to the C=S thioxo function,
an elimination reaction of the protective groups which can be carried by the protected reactive functions,
a salification reaction by a mineral or organic acid or by a mineral or organic base in order to obtain the corresponding salt,
an esterification reaction of the acid function,
a saponification reaction of the ester function to an acid function,
a conversion reaction of the alkoxy function to a hydroxyl function,
a conversion reaction of the cyano function to an acid function,
a reduction reaction of the carboxy function to an alcohol function,
a resolution reaction of the racemic forms.

Under the preferred conditions for the preparation of products of formula I$_{EB}$, the product of formula XII from the products of formulae II$_E$ and XI and the product of formula XIII from the products of formulae II$_F$ and XI can be respectively obtained under the conditions described above for obtaining the product of formula IV from the products of formulae II and III.

The products of formula XIV are obtained by heating in Dowtherm or paraffin at temperatures between 250° C. and 350° C. from the products of formulae XII and XIII, the products of formula XII giving products of formula XIV in which D$_6$ is nitrogen and D$_5$ is methine optionally substituted by R'$_B$, R'$_{2B}$ and R'$_{3B}$ and the products of formula XIII giving products of formula XIV in which D$_5$ is nitrogen and D$_6$ is methine as defined above.

The hydrogenation reaction of the products of formula XIV to products of formula XV can be carried out under the conditions described above for hydrogenation of the products of formula V to products of formula V$_B$ or also of the product of formula IX to product of formula IX$_B$. The decarboxylation reaction of the products of formula XV to products of formula XV' can be carried out under the usual conditions known to one skilled in the art and notably by saponification of the ester in the presence of a base such as sodium or potassium hydroxide, followed by acidification, then heating at a tempeature of about 150° C. to 250° C. in a solvent such as Dowtherm.

The addition of the compound of formula X to the products of formulae XV and XV' to obtain the products of formula I'$_{EB}$ as defined above can be carried out under the conditions for adding the compound of formula X to the products of formulae V, $V_B$, IX or $IX_B$ to obtain the products of formula $I'_B$.

The optional reactions to which the products of formula $I'_{EB}$ are subjected to obtain the products of formula $I_{EB}$ can be carried out under the conditions described for the corresponding reactions to which the products of formula $I'_B$ can be subjected to obtain the products of formula $I_B$.

The compositions of the invention for treating cardiovascular illness are comprised of an amount of at least one compound of formula $I_D$ and their non-toxic, pharmaceutically acceptable salts with acids and bases sufficient to treat cardiovascular illness and an inert pharmaceutical carrier. The compositions may be in the form of tablets, dragees, capsules, granules, suppositories, ointments, creams, gels, aerosols and injectable solutions or suspensions.

The excipient or carrier may be talc, lactose, starch, magnesium stearate, cocoa butter, aqueous or non-aqueous vehicles, fatty bodies of animal or vegetable origin, paraffin derivatives, glycols, various wetting agents, dispersants or emulsifiers and preservatives.

The compositions have antagonistic properties for angiotensin II receptor and are thus notably inhibitors of the effects of angiotensin II, in particular of the vasoconstrictive effect and also of the trophic effect at the level of the myocytes. Some of the products of the present invention also possess antagonistic properties for the endotheline receptor and are thus notably antagonists of the vasoconstrictive effect of endotheline. The compositions also possess the property of improving cognitive functions.

The compositions are useful in the treatment of cardiovascular illness presenting an alteration in the vasomotricity: myocardium infarct, cardiac insufficiency, renal insufficiency, angina pectoris, cerebral vascular spasm, Raynaud's disease, arterial hypertension and all other illnesses following an ischemia. The compositions are also useful for the treatment of glaucoma, atherosclerosis, asthma and various types of visceral spasms, as well as neuronal protective substances or in the prevention of post-angioplastic restenoses.

They are also useful in the treatment of certain gastrointestinal and gynaecological disorders and particularly for a relaxing effect at the level of the uterus and are also useful in the treatment of disorders of the memory and cognitive functions, anxiety, depression, senile dementia and Azheimer's disease.

The novel method of the invention for the treatment of cardiovascular illnesses in warm-blooded animals, including humans, comprises administering to warm-blooded animals an amount of at least one compound of formula $I_D$ and their non-toxic, pharmaceutically acceptable salts with acids and bases sufficient to treat cardiovascular illnesses. The compounds may be administered orally, rectally, parenterally or topically to the skin or mucous membranes. The usual daily dose is 0.013 to 1.33 mg/kg depending on the condition being treated, the specific compound and the method of administration.

The starting compounds of formulae $II_D$, II, $II_E$, $II_F$, III, $VI_D$, VI, VII, X and XI are either commerically available or can be prepared by the usual methods known to one skilled in the art. Among the compounds of formula II which can be found commercially are certain compounds of formula II wherein one of $R'_2$ or $R'_3$ is amino such as methyl-amino-benzoate which is a product marketed by LANCASTER.

Other compounds of formula II which can be found commercially are certain compounds of formula II wherein one of $R'_2$ or $R'_3$ is nitro such as o-nitro-aniline which is product is marketed by UCB. A starting compound of formula $II_D$ is

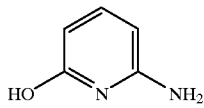

marketed by Columbia and

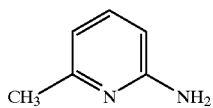

marketed by Aldrich. Starting compounds of formulae $II_E$ and $II_F$ include

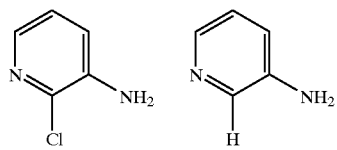

which are marketed by Aldrich. The compounds of formula III may be esters derived from formylacetic acid. Among the examples of such compounds of formula III described in the literature are those in the following references: J. Hel. Chem. Vol. 20, p. 623 to 628 (1983); Liebigs Ann. Chem. Vol. 697 p. 62 to 68 (1966).

The compounds of formulae VI and $VI_D$ may be in particular derivatives of ortho-halo aniline.

Among the preparation of examples of such compounds described in the literature are : Ann. Chim. 1962, Vol. 52, p. 727.

The compounds of formula VII may be in particular derivatives of acetylene. Among the examples of such compounds described in the literature are J. Am. Chem. Soc., 1937, Vol. 58, p. 1490.

Examples of compounds of formula X are describerd in the literature and particularly in U.S. Pat. No. 4,880,804 or U.S. Pat. No. 4,880,804. A preparation process for certain products of formula X as defined above consists of subjecting methyl iodobenzoate to the action of iodotoluene in the presence of powdered copper at a temperature of about 100° C. to 300° C. to obtain a product of the formula

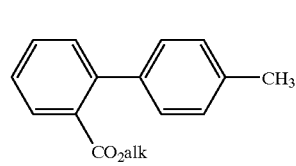

$X_c$

The esterified carboxy can optionally be freed of alkyl by standard methods known to one skilled in the art by acid or alkaline hydrolysis and can be subjected to a bromination reaction on the methyl by standard known methods by the action of N-bromo-succinimide in carbon tetrachloride.

Examples of starting compound of formula XI are

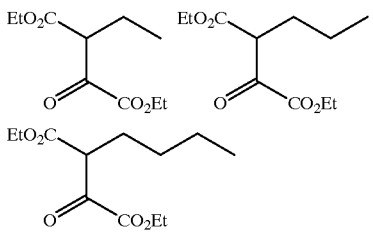

prepared by the reaction

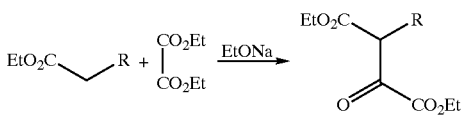

(J. of Het. Chem., Vol. 20 p. 623, 1983) and

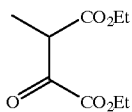

(diethyloxalpropionate) marketed by Aldrich.

An object of the invention are new intermediate products necessary for the preparation of products of formulae $I_D$, $I_E$, $I_B$, $I_G$ and I which are the compounds of formula $IV_D$, IV, $V_D$, V, $IX_D$, IX, $V_{BD}$, $V_B$, $IX_{BD}$, $IX_B$, XII. XIV and XV.

Another object of the invention is the use of the products of

F

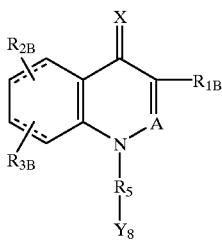

in which:

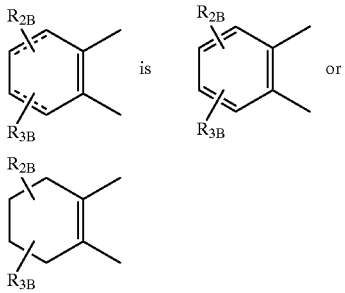

$R_{1B}$ is hydrogen, alkyl, alkenyl or alkynyl of up to 6 carbon atoms, cycloalkyl of 3 to 7 carbon atoms, all optionally substituted, acyl, cyano, free, salified, esterified or amidified carboxy, $R_{2B}$ and $R_{3B}$ are individually selected from the group consisting of
a) hydrogen, halogen, hydroxyl, mercapto, cyano, nitro, sulfo, formyl, benzoy, acyl of 1 to 12 carbon atoms, free, salified or esterified carboxy, cycloalkyl of 3 to 7 carbon atoms, acyloxy of 1 to 12 carbon atoms,
b) alkyl, alkenyl, alkynyl, alkoxy or alkylthio of up to 6 carbon atoms and optionally substituted,
c) aryl, aralkyl, aralkenyl, aryloxy or arylthio in which the alkyl and alkenyl have up to 6 carbon atoms, the aryl being a monocycle of 5 or 6 ring members or condensed rings of 8 to 10 ring members optionally containing at least one heteroatom chosen from oxygen, nitrogen and sulfur and optionally substituted,

in which:
either $R_{6B}$ and $R_{7B}$ or $R_{8B}$ and $R_{9B}$ are individually selected from the group consisting of hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or aralkyl having 2 to 6 alkyl carbon atoms, the aryl being a monocycle of 5 to 6 ring members or condensed rings of 8 to 10 ring members optionally containing at least one heteroatom chosen from oxygen, nitrogen and sulfur and optionally substituted by at least one member chosen from halogen, hydroxyl, cyano, trifluoromethyl, nitro, alkyl, alkenyl, alkoxy, alkylthio and acyl of up to 6 carbon atoms, free, salified or esterified carboxy, $-(CH_2)_{m1}-S(O)_{m2}-Z-R_{14}$, $m_1$ is integer from 0 to 4 and $m_2$ is an integer from 0 to 2, and either $-Z-R_{14}$ is $-NH_2$ or Z is $-N(R_{15})-$, $-N(R_{15})-CO-$, $-N(R_{15})-CO-N(R_{16})-$ or a single bond, and $R_{14}$ is alkyl, alkenyl or aryl optionally substituted, $R_{15}$ and $R_{16}$ are individually hydrogen or $R_{14}$,
or $R_{6B}$ and $R_{7B}$ or $R_{8B}$ and $R_{9B}$ form respectively with the nitrogen atom to which they are attached a monocycle of 5 or 6 ring members or condensed rings of 8 to 10 ring members optionally containing one or more heteroatoms chosen from oxygen, nitrogen and sulfur and optionally substituted by at least one member chosen from halogen, hydroxyl, cyano, trifluoromethyl, nitro, alkyl, alkenyl, alkoxy, alkylthio and acyl of up to 6 carbon atoms, free, salified or esterified carboxy,
or $R_{8B}$ and $R_{9B}$ individually are an acyl of a carboxylic acid of up to 6 carbon atoms,
c) $-(CH_2)_{m1}-S(O)_{m2}-Z-R_{14}$ as defined above,
X is oxygen or sulfur,
A is nitrogen or $=C-R_4$, $R_4$ has the same values of $R_1$, it being understood that when A is nitrogen or $=C-H$, $R_1$ is not hydrogen,
$R_5$ is divalent alkylene of 1 to 4 carbon atoms,
$Y_A$ is $-Y_{1B}-B-Y_{2B}$,
$Y_{1B}$ is monocyclic aryl of 5 or 6 ring members or condensed rings of 8 to 10 ring members optionally containing at least one heteroatom chosen from oxygen, nitrogen and sulfur and optionally substituted by at least one of $R_{2B}$ or $R_{3B}$,
B is either a single bond between $Y_{1B}$ and $Y_{2B}$, or $-CO-$, $-NH-CO-$, $-CO-NH-$, $-O-(CH_2)_n$ or $-S-(CH_2)_n$, n is an integer of 0 to 4,
$Y_{2B}$ is if B is a single bond, hydrogen, halogen, hydroxyl, cyano, nitro, trifluoromethyl, free, salified or esterified carboxy, tetrazole or isoxazole, or if B is other than a single bond, $Y_{2B}$ has the values for $Y_{1B}$, the said products of formula F being in all possible racemic, enantiomeric and diastereoisomeric isomer forms, as well as their addition salts with mineral and organic acids or mineral and organic bases of the said products of formula F for the preparation of medicaments, intended either for the treatment of arterial hypertension, cardiac insufficiencies, renal insufficiencies and in the prevention of post-angioplastic restenoses, or for the treatment of certain gastrointestnal or gynaecological disorders, or for the treatment of disorders of the memory and cognitive functions, anxiety, depression, senile dementia and Alzheimer's disease.

A particular subject of the present invention is the use of the products of formulae $I_D$ and F in the preparation of medicaments intended for treatment of arterial hypertension, cardiac insufficiencies, renal insufficiencies, in the prevention of postangioplastic restenoses, as well as in the treatment of various forms of vascular spasms or for the treatment of disorders of the memory and cognitive functions, anxiety, depression, senile dementia and Alzheimer's disease.

In the following examples, there are described several preferred embodiments to illustrate the invention. However, it is to be understood that the invention is not intended to be limited to the specific embodiments.

EXAMPLE 1

4-(3-butyl-1,4-dihydro-4-oxo-quinolinyl methyl)-benzonitrile

STEP A: Diethyl 2-butyl-3-oxo-butanedioate 13.55 ml of diethyl oxalate were added to a suspension of sodium ethylate (prepared by stirring for one hour at 40° C. of 2.3 g of sodium and 150 ml of ethanol, then evaporation of the solvent) in 100 ml of ether and the mixture was refluxed for 15 minutes, cooled down slightly and 50 ml of ethyl caproate were added. The mixture was stirred for 3 hours at reflux and for 16 hours at 30° C. to 35° C. 50 ml of water were added and the aqueous phase was separated by decanting, washed twice with ether and acidified with 2N hydrochloric acid. Extraction was carried out 3 times with ether and the organic phases were washed with water, then with a saturated solution of sodium chloride, dried and evaporated to dryness to obtain 9.5 g of the desired product which was used as is for the following step.

STEP B: Diethyl 2-butyl-3-(phenylamino)-2-butenedioate

A mixture of 1 g of aniline with 2.65 g of the product of Step A and 150 mg of Siliporite$^R$ NK10 was stirred for 3 days at 75° C. and then the reaction mixture was cooled down and chromatographed on silica (eluant: hexane-ethyl acetate (9-1) to obtain 1.55 g of the expected product.

| IR Spectrum (in CHCl$_3$): | |
|---|---|
| =C—NH | 3260 cm$^{-1}$ |
| C=O | 1733–1656 cm$^{-1}$ |
| C=C + | 1610 cm$^{-1}$ (shoulder) |
| Aromatics | 1596 cm$^{-1}$ |
| | 1584 cm$^{-1}$ |
| | 1500 cm$^{-1}$ |

STEP C: Ethyl 3-butyl-4-hydroxy-2-quinoline carboxylate and ethyl 3-butyl-1,4-dihydro-4-oxo-2-quinoline carboxylate A mixture of 2.5 g of the product of Step B with 30 ml of diphenyl ether was heated for 30 minutes in a bath at 250° C. and the mixture was allowed to return to ambient temperature, separated and washed with pentane to obtain 1.82 g of the desired product.

| IR Spectrum (in CHCl$_3$): | |
|---|---|
| =C—NH | 3425–3383 cm$^{-1}$ |
| C=O | 1746–1706 cm$^{-1}$ (F) |
| other C=O | 1624 cm$^{-1}$ |
| C=C + | 1605 cm$^{-1}$ |
| Aromatics | 1585 cm$^{-1}$ |
| | 1572 cm$^{-1}$ |
| | 1532 cm$^{-1}$ |

STEP D: 3-butyl-1,4-dihydro-4-oxo-2-quinoline carboxylic acid 1.8 g of the ester of Step C with 25 ml of N sodium hydroxide solution washeated for one hour at 60° C. and the mixture was cooled down and acidified with N hydrochloric acid and filtered. The residue was washed with water and dried at 60° C. under reduced pressure to obtain 1.58 g of the desired product.

| NMR Spectrum 60 MHz (D.M.S.O. 0 ppm | |
|---|---|
| C$\underline{H}_3$—CH$_2$—CH$_2$—CH$_2$— | 0.89(t) |
| C—$\underline{C}$—$\underline{C}$—C | 1.39(m) |
| C—C—C—$\underline{C}$— | 2.78 |
| H$_6$ and H$_7$ | 7.30(t)–7.63(t) |
| H$_5$ and H$_8$ | 7.80(d)–8.08(d) |
| Mobile proton | 11.64 |

STEP E: 3-butyl-4-(1H)-quinolinone

A mixture of 1.55 g of the product of Step D and 10 ml of diphenyl ether was heated for 30 minutes at 250° C. and the mixture was cooled down, filtered. The residue is washed with pentane and dried under reduced pressure to obtain 1.17 g of product which was dissolved in 80 ml of ethanol and treated for 15 minutes at reflux in the presence of activated charcoal. Filtration was carried out on hyfluosupercel and the ethanol was evaporated to dryness. The residue was taken up in pentane, filtered, washed with pentane and dried at 50° C. under reduced pressure to obtain 971 mg of the desired product.

| IR Spectrum (in CHCl$_3$): (mixture of two forms: enol and keto) | |
|---|---|
| =C—NH | 3440 cm$^{-1}$ + general absorption |
| C=O | 1632 cm$^{-1}$ |
| C=C + | 1590 cm$^{-1}$ |
| Aromatics | 1570 cm$^{-1}$ (shoulder) |
| | 1558 cm$^{-1}$ |
| | 1524 cm$^{-1}$ |
| | 1506 cm$^{-1}$ |

STEP F: 4-(3-butyl-1,4-dihydro-4-oxo-quinolinyl methyl)-benzonitrile 3.3 g of activated potassium carbonate were added to a suspension of 2.3 g of the product of Step E in 50 ml of acetone a the mixture was stirred for 10 minutes. Then, 4.7 g of 4-bromobenzonitrile were added, followed by heating for 4 hours at reflux. The acetone was evaporated off and the residue was taken up in 100 ml of water. Extraction was carried out with ethyl acetate and the extracts were washed with a saturated solution of ammonium chloride, dried and evaporated to dryness to obtain 4.1 g of the expected product which was chromatographed on silica (eluant: methylene chloride-methanol (98-2)) to obtain 3.3 g of the desired product melting at 168° C.

| IR Spectrum (CHCl$_3$): | |
| --- | --- |
| Absence of NH | |
| C≡N | 2235 cm$^{-1}$ |
| C=O | 1630 cm$^{-1}$ |
| C=C + | 1587 cm$^{-1}$ |
| Aromatic | 1558 cm$^{-1}$ |
| | 1510 cm$^{-1}$ |
| | 1490 cm$^{-1}$ |

EXAMPLE 2

4-[(3-butyl-1,4-dihydro-4-oxo-1-quinolinyl)-methyl]-benzoic acid

A mixture of 0.5 g of the product of Example 1 with 8 ml of ethanol and 1.6 ml of 5N sodium hydroxide solution was refluxed with stirring for 4 hours and then was cooled down to 0° C. and acidified with concentrated hydrochloric acid. The mixture was stirred for one night at 0° C., followed by separating, washing with water, drying and evaporating to dryness to obtain 0.48 g of product which was crystallized from 20 ml of ethanol to obtain 275 mg of the desired product melting at 224° C.

Analysis: C$_{21}$H$_{21}$NO$_3$; molecular weight=335.41 Calculated: % C 75.20 % H 6.31 % N 4.17 Found: 75.3 6.3 4.1

| IR Spectrum (CHCl$_3$): | |
| --- | --- |
| Absence C=N | |
| Acid OH type absorption complex | |
| C=O | 1699 cm$^{-1}$ |
| —C=C + | 1623 cm$^{-1}$ |
| Aromatics | 1614 cm$^{-1}$ |
| other C=O's | 1562 cm$^{-1}$ |
| | 1535 cm$^{-1}$ |
| | 1494 cm$^{-1}$ |

EXAMPLE 3

Methyl 4'-[(3-butyl-1,4-dihydro-4-oxo-1-quinolinyl)-methyl](1,1'-biphenyl)-2-carboxylate Using the procedure of Example 1, 4.02 g of the compound of Step E of Example 1 and 5.52 g of potassium carbonate and 6.2 g of methyl bromomethyl-(1,1'biphenyl)-2-carboxylate (preparation according to EP 0,253,310) were reacted to obtain after chromatography on silica (eluant: methylene chloride-methanol (98-2)), 8 g of the desired product.

| IR Spectrum (CHCl$_3$): | |
| --- | --- |
| O‖—C—CH$_3$ | 1723 cm$^{-1}$ |
| | 1437 cm$^{-1}$ |

| IR Spectrum (CHCl$_3$): | |
| --- | --- |
| Other C=O | 1628 cm$^{-1}$ |
| C=C + | 1583 cm$^{-1}$ |
| Aromatic | 1556 cm$^{-1}$ |
| | 1492 cm$^{-1}$ |

EXAMPLE 4

4'-[(3-butyl-1,4-dihydro-4-oxo-1-quinolinyl)-methyl](1,1'-biphenyl)-2-carboxylic acid Using the procedure of Example 2, 0.48 g of the product of Example 3 were reacted to obtian after crystallization from ethanol 0.240 g of the desired product melting at 214° C.

Analysis: C$_{27}$H$_{25}$NO$_3$; molecular weight=411.51 Calculated: % C 78.8 % H 6.12 % N 3.403 Found: 78.7 6.1 3.4

| IR Spectrum (CHCl$_3$): | |
| --- | --- |
| Absorption complex OH/NH region | |
| C=O | 1665–1615 cm$^{-1}$ |
| —C=C + | 1602 cm$^{-1}$ |
| Aromatics | 1560 cm$^{-1}$ |
| | 1530 cm$^{-1}$ |

EXAMPLE 5

Methyl 4'-[(3-butyl-1,4-dihydro-4-thioxo-1-quinolinyl)-methyl](1,1'-biphenyl)-2-carboxylate 2.10 mg of Lawesson reagent were added to a solution of 400 mg of the product of Example 3 in 20 ml of toluene and the mixture was refluxed for 90 minutes. The mixture was poured into 100 ml of water and extraction was carried out with ethyl acetate. Th extracts were washed with water, dried, filtered and evaporated to dryness to obtain 0.6 g of the expected product which was chromatographed on silica (eluant: methylene chloride-acetone (98-2)) to collect 0.42 g of the desired product melting at 158° C.

| IR Spectrum (CDCl$_3$): | |
| --- | --- |
| C=0 (ester) | 1724 cm$^{-1}$ |
| Conjugated system | 1616 cm$^{-1}$ |
| + | 1601 cm$^{-1}$ |
| Aromatic | 1548 cm$^{-1}$ |
| | 1499 cm$^{-1}$ |

EXAMPLE 6

4'-[(3-butyl-1,4-dihydro-4-thioxo-1-quinolinyl)-methyl (1,1'-biphenyl)-2-carboxylic acid Using the procedure of Example 2, 400 mg of product of Example 5 and 15 ml of concentrated sodium hydroxide were reacted to obtain 0.35 g of crude product melting at >260° C. After crystallization from ethanol, 270 mg of the desired product melting at >260° C. were obtained.

Analysis: C$_{27}$H$_{25}$NO$_2$S ; molecular weight=427.57 Calculated: % C 75.85 % H 5.89 % N 3.27 % S 7.5 Found: 75.7 5.8 3.2 7.5

| IR Spectrum (Nujol) | |
|---|---|
| Acid OH region absorption | |
| C=O | 1701 – 1675 cm$^{-1}$ |
| | 1612 cm$^{-1}$ |
| C=C | 1602 cm$^{-1}$ |
| + | 1574 cm$^{-1}$ |
| Aromatics | 1545 cm$^{-1}$ |
| | 1500 cm$^{-1}$ |

EXAMPLE 7

Methyl4-'[(3-butyl-1,4-dihydro-5-methylthio-4-oxo-1-quinolinyl)-methyl]1,1'-biphenyl-2-carboxylate

STEP A: Diethyl 2-butyl-3-[[(3-methylthio)-phenyl]-amino]-2-butenedioate 50 mg of p-toluene sulfonic acid were added to a solution of 4.3 g of the product of Step A of Example 1 with 2 ml of 3-methyl mercapto aniline in 100 ml of toluene and the mixture was stirred for 4 hours at reflux, eliminating the water formed. After evaporation to dryness, the residue was chromatographed on silica (eluant: methylene chloride with 30% hexane) to obtain 5.1 g of the desired product melting at 55° C.

| IR Spectrum (CHCl$_3$): | |
|---|---|
| =C—NH complex | 3240 cm$^{-1}$ |
| C=O | 1732 – 1658 cm$^{-1}$ |
| C=C | 1598 cm$^{-1}$ |
| + | 1583 cm$^{-1}$ |
| Aromatics | 1488 cm$^{-1}$ |

STEP B: Ethyl 3-butyl-1,4-dihydro-5-(methylthio)-4-oxo-2-quinoline carboxylate 1 g of the product of Step A was heated for 45 minutes at 250° C. and after cooling, the crude reaction product was chromatographed on silica (eluant: methylene chloride) to obtain 700 mg of the desired product melting at 80° C.

| IR Spectrum (CHCl$_3$): | |
|---|---|
| NH complex | 3330 cm$^{-1}$ (F) |
| C=O | 1743 cm$^{-1}$ |
| | 1707 (F) |
| C=O | 1610 cm$^{-1}$ |
| + | |
| C=C | 1596 CM$^{-1}$ |
| + | 1559 cm$^{-1}$ |
| Aromatics | 1530 cm$^{-1}$ |

STEP C: 3-butyl-1,4-dihydro-5-(methylthio)-4-oxo-2-quinoline carboxylic acid hydrochloride 0.63 g of the product of Step B in 10 ml of a N sodium hydroxide solution was stirred for 2 hours at reflux and the mixture was poured into ice-cooled water, acidified with concentrated hydrochloric acid, separated, washed with water, dried and impasted in 100 ml of ethyl acetate to obtain 495 mg of the desired product melting at 240° C.

| IR Spectrum (Nujol): | |
|---|---|
| OH/NH absorption | 3328 cm$^{-1}$ |
| C=O | 1744 cm$^{-1}$ |
| C=O | 1610 cm$^{-1}$ |
| + | 1592 cm$^{-1}$ |
| C=C | 1560 cm$^{-1}$ |
| + | 1540 cm$^{-1}$ |
| Aromatic | 1516 cm$^{-1}$ |

STEP D: 3-butyl-5-(methylthio)-4-(1H)-quinolinone 390 mg of the product of Step C were heated for 5 minutes at 260° C. to obtain 300 mg of the desired product melting at 144° C.

| IR Spectrum (CHCl$_3$): | |
|---|---|
| =C—NH | 3365 cm$^{-1}$ |
| C=O | 1627 cm$^{-1}$ |
| + | 1609 cm$^{-1}$ |
| C=C | 1585 cm$^{-1}$ |
| + | 1560 cm$^{-1}$ |
| Aromatic | 1520 cm$^{-1}$ |

STEP E: Methyl 4'-[[3-butyl-1,4-dihydro-5-(methylthio)-4-oxo-1-quinolinyl]-methyl](1,1'-biphenyl)-2-carboxylate Using the procedure of Example 1, 1.1 g of the product of Step D and 1.63 g of methyl 4-bromomethyl (1,1'-biphenyl) 2-carboxylate (prepared according to EP 0,253,310) and 1.2 g of potassium carbonate were reacted to obtain after chromatography on silica (eluant: ethyl acetate-hexane (5-5)), 270 mg of the expected product.

| NMR Spectrum (CDCl$_3$) 250 MHz | |
|---|---|
| C$\underline{H_3}$—(CH$_2$)$_2$—CH$_2$—C— | 0.91 (T) |
| CH$_3$—C$\underline{H_2}$—CH$_2$—CH$_2$—C— | 1.36 (m) |
| CH$_3$—CH$_2$—C$\underline{H_2}$—CH$_2$—C | 1.58 (m) |
| CH$_3$—(CH$_2$)$_2$—C$\underline{H_2}$—C— | 2.56 (m) |
| SCH$_3$ | 2.37 (s) |
| N—C$\underline{H}$=C | 7.47 (s) |
| N—C$\underline{H_2}$—C$_6$H$_4$ | 5.99 (o) |
| CO$_2$—C$\underline{H_3}$ | 3.57 (o) |

EXAMPLE 8

4'-[(3-butyl-1,4-dihydro-5-(methylthio)-4-oxo-1-quinolinyl)-methyl](1,1'-biphenyl)-2-carboxylic acid A mixture of 270 mg of the product of Example 7, 5 ml of a 5N sodium hydroxide solution and 5 ml of ethanol was stirred for 2 hours at reflux and the mixture was poured into water and acidified with sodium hydrogen phosphate. Extraction was carried out with ethyl acetate and the extracts were washed with water, dried and evaporated to dryness. The residue was chromatographed on silica (eluant: methylene chloride-methanol (9-1)) and the product was impasted in a mixture of 5 ml of ethyl acetate and 5 ml of isopropyl ether to obtain 90 mg of the desired compound melting at 155° C.

Analysis: C$_{28}$H$_{27}$NO$_3$S; molecular weight=457.60 Calculated: % C 73.5 % H 5.95 % N 3.06 % S 7.00 Found: 73.5 5.8 3.2 6.8

| IR Spectrum (CHCl₃): | |
|---|---|
| C=O | 1728 cm⁻¹ (sh) acid |
| | 1698 cm⁻¹ (max) |
| C=O + | 1624 cm⁻¹ |
| C=C + | 1604 cm⁻¹ 1577 cm⁻¹ |
| Aromatics | 1542 cm⁻¹ |

EXAMPLE 9

Methyl 3-butyl-1-[(2'-methoxy carbonyl-1,1'-biphenyl-4-yl)-methyl]-1,4-dihydro-4-oxo-7-quinoline carboxylate

STEP A: Diethyl 2-butyl-3-[[3-(methoxycarbonyl)-phenyl]-amino]-2-butenedioate A solution of 3.02 g of methyl m-amino-benzoate and 4.9 g of diethyl 2-butyl-3-oxo butanedioate of Step A of Example 1 in 100 ml of toluene was prepared to which 20 mg of p-toluene sulfonic acid were added. The mixture was stirred at reflux for about 4 hours and after evaporation to dryness, the residue was chromatographed on silica (eluant: ethyl acetate-hexane (2-8)) to obtain 6.5 g of the expected product.

| IR Spectrum (CHCl₃): | |
|---|---|
| =C—NH complex | approx. 3250 cm⁻¹ |
| C=O | 1725 cm⁻¹ conjugated esters |
| of which C—OCH₃ with CH₃ | 1438 cm⁻¹ |
| C=O | 1655 cm⁻¹ chelated ester |
| C=C + | 1596 cm⁻¹ (F) |
| Aromatic | 1493 cm⁻¹ |

STEP B: 2-ethyl-7-methyl-3-butyl-1,4-dihydro-4-oxo-2,7-quinoline dicarboxylate Using the procedure of Step B of Example 7, 6 g of the product of Step A were reacted to obtain after chromatography on silica (eluant: ethyl acetate-hexane (4-6), 1.8 g of the expected product melting at 210° C.

| IR Spectrum (CHCl₃): | |
|---|---|
| | 3422 cm⁻¹ |
| =C—NH | 3377 cm⁻¹ |
| C=O complex | Max: 1724 cm⁻¹ (esters) |
| C=O region | 1631 cm⁻¹ |
| C=C + | 1605 cm⁻¹ |
| | 1569 cm⁻¹ |
| Aromatics | 1537 cm⁻¹ |
| CH₃ of CO₂CH₃ | 1439 cm⁻¹ |

STEP C: 3-butyl-1,4-dihydro-4-oxo-2,7-quinoline dicarboxylic acid

Using the procedure of Step C of Example 7, 1.8 g of product of Step B were reacted to obtain 1.27 g of the expected product melting > to 260° C.

| IR Spectrum (Nujol): | |
|---|---|
| OH/NH region | Max 3385 cm⁻¹ |
| | 3280 cm⁻¹ + general absorption |
| C=O | 1688 cm⁻¹ complex |
| C=C | 1631 cm⁻¹ |
| + | 1593 cm⁻¹ |
| Aromatics | 1550 cm⁻¹ 1520 cm⁻¹ |

STEP D: 3-butyl-1,4-dihydro-4-oxo-7-quinoline carboxylic acid

Using the procedure of Step D of Example 7, 1.23 g of the product of Step C were reacted to obtain 1 g of the expected product melting > at 260° C.

| IR Spectrum (Nujol): | |
|---|---|
| OH/NH region complex absorption | |
| C=O | 1710 cm⁻¹ |
| | 1692 cm⁻¹ |
| | 1640 cm⁻¹ |
| C=C | 1619 cm⁻¹ |
| + | 1594 cm⁻¹ |
| Aromatics | 1570 cm⁻¹ |
| | 1517 cm⁻¹ |

STEP E: Methyl 3-butyl-1,4-dihydro-4-oxo-7-quinoline carboxylate

Diazomethane was added to a solution in methylene chloride of the product of Step D until a persistent yellow color was obtained. The excess diazomethane was destroyed with acetic acid and the medium was evaporated t dryness to obtain the expected product.

STEP F: Methyl 3-butyl-1-[[2'-(methoxycarbonyl)(1,1'-biphenyl)-4-yl]-methyl]-1,4-dihydro-4-oxo-7-quinoline carboxylate Using the procedure of Example 1, 220 mg of the product of Step E and 285 mg of methyl bromomethyl (1,1'-biphenyl) 2-carboxylate (preparation according to EP 0,253, 310) were reacted to obtain after chromatography on silica (eluant: methylene chloride-acetonitrile 87-13), 340 mg of the desired product.

| IR Spectrum (CHCl₃): | |
|---|---|
| C=O | 1723 cm⁻¹ (F) esterr |
| C=O | 1631 cm⁻¹ |
| + | 1590 cm⁻¹ |
| Aromatic | 1548 cm⁻¹ |
| + | 1514 cm⁻¹ |
| C=C | 1495 cm⁻¹ |

EXAMPLE 10

3-butyl-1-[[2'-carboxy-(1,1'-biphenyl)-4-yl]-methyl]-1,4-dihydro-4-oxo-7-quinoline carboxylic acid Using the procedure of Example 2, 290 mg of the product of Example 9 and 5 ml of a 5N sodium hydroxide solution were reacted to obtain 210 mg of the desired product melting at >260° C.

Analysis: $C_{28}H_{25}NO_5$; molecular weight=455.515 Calculated: % C 73.83 % H 5.53 % N 3.07 Found: 73.7 5.5 3.0

IR Spectrum (Nujol):

| | |
|---|---|
| OH/NH general absorption | 1706 cm$^{-1}$ |
| C=O | 1628 cm$^{-1}$ |
| C=C | 1590 cm$^{-1}$ |
| + | 1576 cm$^{-1}$ |
| Aromatics | 1540 cm$^{-1}$ 1498 cm$^{-1}$ |

EXAMPLE 11

Methyl 4'-[[3-butyl-1,4-dihydro-7-(hydroxymethyl)-4-oxo-1-quinolinyl]-methyl](1,1'-biphenyl)-2-carboxylate

STEP A: 3-butyl-7-hydroxy-methyl-4-(1H)-quinolinone 35 mg of aluminium-lithium hydride were added to a solution of 240 mg of the product of Step E of Example 9 in 50 ml of tetrahydrofuran, and the mixture was stirred for 30 minutes at ambient temperature. Tetrahydrofuran with 10% water, then 50 ml of water were added and extraction was carried out with ethyl acetate. The extracts were washed with water, dried and evaporated to dryness. After chromatography on silica (eluant: methylene chloride-methanol (9-1)), 170 mg of the desired product were obtained melting at 200° C.

IR Spectrum (Nujol):

| | |
|---|---|
| Absence of C=O ester | |
| Complex absorption OH/NH regions | |
| Aromatics | 1640 cm$^{-1}$ |
| C=C | 1616 cm$^{-1}$ |
| C=O | 1558 cm$^{-1}$ 1526 cm$^{-1}$ 1503 cm$^{-1}$ |

STEP B: Methyl 4'-[[3-butyl-1,4-dihydro-7-(hydroxymethyl)-4-oxo-1-quinolinyl]-methyl](1,1'-biphenyl)-2-carboxylate Using the procedure of Example 1, 160 mg of the product of Step A and 260 mg of methyl bromomethyl (1,1'-biphenyl)-2-carboxylate (preparation according to EP 0,253,310) were reacted to obtain after chromatography on silica (eluant: methylene chloride-methanol (95-5)), 280 mg of the desired product melting at 140° C.

IR Spectrum (CHCl$_3$):

| | |
|---|---|
| OH | 3610 cm$^{-1}$ + associated (strong) |
| C=O | 1719 cm$^{-1}$ ester |
| | 1628 cm$^{-1}$ conjugated ketone |
| C=C + | 1583 cm$^{-1}$ 1548 cm$^{-1}$ |
| Aromatics | 1518 cm$^{-1}$ 1501 cm$^{-1}$ |

EXAMPLE 12

4'-[[3-butyl-1,4-dihydro-7-(hydroxymethyl)-4-oxo-1-quinolinyl]-methyl (1,1'-biphenyl) 2-carboxylic acid Using the procedure of Example 2, 280 mg of the product of Example 11 and 5 ml of a normal solution of sodium hydroxide were reacted to obtain after crystallization from ethanol with 50% water, 200 mg of the desired product melting at 212° C.

Analysis: C$_{28}$H$_{27}$NO$_4$; molecular weight=441.5 Calculated: % C 76.17 % H 6.16 % N 3.17 Found: 76.4 6.0 3.1

IR Spectrum (CHCl$_3$):

| | |
|---|---|
| General absorption OH/NH | |
| | 1727 cm$^{-1}$ (F) 1714 cm$^{-1}$ |
| C=O | 1626 cm$^{-1}$ |
| conjugated C=O | |
| + | 1618 cm$^{-1}$ |
| Aromatics | 1527 cm$^{-1}$ 1506$^{-1}$ |
| | 1492 cm$^{-1}$ |

EXAMPLE 13

4-[(3-butyl-1,4-dihydro-4-oxo-1-cinnolinyl)-methyl]-benzonitrile

STEP A: 2-(1-hexynyl) benzene amine 32 mg of copper iodide and 140 mg of bis(triphenylphosphine) palladium chloride, then 2.3 ml of 1-hexyne were added to a solution of 4.4 g of 2-iodoaniline in 100 ml of triethylamine and the mixture was stirred for 15 hours at ambient temperature. After evaporation to dryness, the residue was taken up in ether and the insoluble part was filtered out and washed with ether. The filtrate was evaporated to dryness and the residue was chromatographed on silica (eluant: hexane-ethyl acetate (9-1)) to obtain 3.27 g of the desired product.

IR Spectrum (CHCl$_3$):

| | |
|---|---|
| | 3486 cm$^{-1}$ |
| —C$_6$H$_4$—NH$_2$ | 3390 cm$^{-1}$ |
| NH$_2$ def | 1613 cm$^{-1}$ |
| + | 1570 cm$^{-1}$ |
| Aromatic | 1493 cm$^{-1}$ |

STEP B: 3-butyl-4-hydroxy cinnoline

A solution of 2 g of sodium nitrite in 60 ml of water was added at 0° C. to a suspension prepared at 0° C. of 3.2 g of the product of Step A in 100 ml of concentrated hydrochloric acid and the mixture was stirred for 90 minutes at 0° C., then for one hour at 100° C. The cooled reaction mixture was poured into 100 ml of ice-cooled water and after separating and washing with water, the moist crude product was taken up in 100 ml of water, alkalinized with concentrated ammonium hydroxide, separated and washed with water to obtain after drying at 70° C., 1.47 g of the desired product melting at 180° C.

IR Spectrum (Nujol):

| | |
|---|---|
| Absorption NH/OH region | |
| C=C | 1636 cm$^{-1}$ |
| + | 1604 cm$^{-1}$ |
| Aromatics | 1580 cm$^{-1}$ |
| | 1578 cm$^{-1}$ |
| | 1498 cm$^{-1}$ |

STEP C: 4-[[3-butyl-1,4-dihydro-4-oxo-1-cinnolinyl]-methyl]-benzonitrile

Using the procedure of Example 1, 406 mg of the product of Step B and 430 mg of 4-bromomethyl benzonitrile and 830 mg of potassium carbonate were reacted to obtain after chromatography on silica (eluant: methylene chloride-methanol (98-2)), 460 mg of the desired product melting at 180° C.

| IR Spectrum (CHCl$_3$): | |
|---|---|
| Absence of OH | |
| conjugated C≡N | 2233 cm$^{-1}$ |
| C═C | 1622 cm$^{-1}$ |
| C═N | 1606 cm$^{-1}$ |
| Aromatics | 1574 cm$^{-1}$ |
| C═O | 1526 cm$^{-1}$ |
| | 1510 cm$^{-1}$ |

EXAMPLE 14

4-[[3-butyl-1,4-dihydro-4-oxo-1-cinnolinyl]-methyl]-benzoic acid

Using the procedure of Example 2, 400 mg of the product of Example 13 and 4 ml of a 5N sodium hydroxide solution were reacted to obtain 400 mg of the expected product melting at 220° C. After crystallization from 50 ml of acetonitrile, 270 mg of the purified product melted at 220° C.

Analysis: C$_{20}$H$_{20}$N$_2$O$_3$; molecular weight=336.393 Calculated: % C 71.41 % H 5.99 % N 8.33 Found: 71.3 6.0 8.3

| IR Spectrum (Nujol): | |
|---|---|
| Absence of C═N | |
| Acid with C═O | 1700 cm$^{-1}$ |
| Aromatic | 1609 cm$^{-1}$ (sh) |
| + | 1596 cm$^{-1}$ |
| Heteroatom | 1577 cm$^{-1}$ |
| | 1523 cm$^{-1}$ |
| | 1490 cm$^{-1}$ |

EXAMPLE 15

Methyl 4'-[[3-butyl-1,4-dihydro-4-oxo-7-[(1-pyrrolidinyl)-carbonyl]-1-quinolinyl]-methyl](1,1'-biphenyl)-2-carboxylate STEP A: 3-butyl-1,4-dihydro-4-oxo-7-[(1-pyrrolidinyl)-carbonyl quinoline A suspension of 1.52 g of the product of Step D of Example 9 in 100 ml of tetrahydrofuran was prepared to which 0.65 ml of pyrrolidine were added. The reaction medium was cooled to 0° C. and 1 ml of triethylamine, 100 ml of methylene chloride, 1 g of hydroxy-benzotriazole and 1.82 g of 1-(3-dimethylaminopropyl)-3-ethyl carbodiimide hydrochloride were added to it successively. The medium was stirred for 3 hours at ambient temperature and ice-cooled water was added, followed by acidifying to pH=5–6 with 0.1N hydrochloric acid. The organic phase was washed with water, dried and evaporated to dryness. The residue was chromatography on silica (eluant: methylene chloride-methanol (9-1) to obtain 1.8 g of the expected product.

| IR Spectrum (CHCl$_3$): | |
|---|---|
| | 3430 cm$^{-1}$ |
| | 3240 cm$^{-1}$ |

| IR Spectrum (CHCl$_3$): | |
|---|---|
| NH absorption complex | 3190 cm$^{-1}$ |
| | 3139 cm$^{-1}$ |
| | 3090 cm$^{-1}$ |
| C═O + | 1638 cm$^{-1}$ |
| Aromatic + | 1605 cm$^{-1}$ (complex) |
| Heterocycle | |

STEP B: Methyl 4'-[[3-butyl-1,4-dihydro-4-oxo-7-[(1-pyrrolidinyl)-carbonyl]-1-quinolinyl]-methyl](1,1'-biphenyl)-2-carboxylate Using the procedure of Example 3, 500 mg of the product of Step A were reacted to obtain 0.675 g of the expected product melting at 191° C. after impasting in isopropyl ether.

| IR Spectrum (CHCl$_3$): | |
|---|---|
| C═O (ester) | 1723 cm$^{-1}$ |
| Other C═O | 1618 cm$^{-1}$ (complex) |
| + | 1588 cm$^{-1}$ |
| Aromatic + | 1543 cm$^{-1}$ |
| Heterocycle | 1498 cm$^{-1}$ |

EXAMPLE 16

4'-[[3-buty-1,4-dihydro-4-oxo-7-[1-pyrrolidinyl)-carbonyl]-1-quinolinyl]-methyl](1,1'-biphenyl)-2-carboxylic acid Using the procedure of Example 2, 1.1 g of the product of Example 15 were reacted to obtain after crystallization from ethanol, 0.67 g of the expected product melting at >260° C.

| IR Spectrum (Nujol): | |
|---|---|
| Absorption OH/NH region | |
| C═O | 1714 cm$^{-1}$ (sh) |
| | 1695 cm$^{-1}$ (max) |
| | 1618 cm$^{-1}$ (sh) |
| | 1607 cm$^{-1}$ (max) |
| Aromatic | 1598 cm$^{-1}$ |
| + | 1563 cm$^{-1}$ |
| Heteroaromatic | 1524 cm$^{-1}$ |
| | 1500 cm$^{-1}$ |

Analysis: C$_{32}$H$_{32}$N$_2$O$_4$; molecular weight=508.62 Calculated: % C 75.57 % H 6.34 % N 5.51 Found: 75.4 6.2 5.3

EXAMPLE 17

Methyl 4'-[(3-butyl-1,4-dihydro-8-bromo-4-oxo-1-quinolinyl)-methyl]1,1'-biphenyl-carboxylate STEP A: Diethyl 2-butyl-3-[[2-bromophenyl]-amino]-2-butenedioate A solution of 5 g of bromoaniline and 7.9 g of diethyl 2-buty-3-oxo-butanedioate in 100 ml of toluene and 100 mg of p-toluene sulfonic acid was stirred for 4 hours at reflux and after evaporation to dryness, the residue was chromatographed on silica (eluant: methylene chloride-hexane (6-4)) to obtain 7.2 g of the desired product.

| IR Spectrum (CHCl$_3$): | |
|---|---|
| NH | 3230 cm$^{-1}$ |
| C=O | 1732 cm$^{-1}$ – 1658 cm$^{-1}$ |
| C=C | 1600 cm$^{-1}$ |
| + | 1572 cm$^{-1}$ |
| Aromatic | 1490 cm$^{-1}$ |

STEP B: Ethyl 3-butyl-1,4-dihydro-8-bromo-4-oxo-2-quinoline carboxylate

Using the procedure of Step B of Example 7, 7 g of the product of Step A were reacted to obtain after chromatography on silica (eluant: methylene-chloride), 6.3 g of the expected product melting at 88° C.

| IR Spectrum (CHCl$_3$): | |
|---|---|
| =C—NH | 3398 cm$^{-1}$ – 3350 cm$^{-1}$ |
| C=O | 1744 cm$^{-1}$ – 1708 cm$^{-1}$ |
| C=O + | 1620 cm$^{-1}$ |
| C=C + | 1598 cm$^{-1}$ |
| Aromatic | 1558 cm$^{-1}$ |
| | 1530 cm$^{-1}$ |

STEP C: 3-butyl-1,4-dihydro-8-bromo-4-oxo-2-quinoline carboxylic acid

Using the procedure of Step C of Example 7, 6.3 g of the product of Step B were reacted to obtain 6 g of the desired product melting at 220° C.

| IR Spectrum (Nujol): | |
|---|---|
| OH/NH absorption | 3376 cm$^{-1}$ – 3316 cm$^{-1}$ |
| —C=O | 1734 cm$^{-1}$ – 1704 cm$^{-1}$ |
| C=O | 1618 cm$^{-1}$ |
| + | 1590 cm$^{-1}$ |
| C=C | 1560 cm$^{-1}$ |
| + | 1542 cm$^{-1}$ |
| Aromatic | 1518 cm$^{-1}$ |

STEP D: 3-butyl-8-bromo-4-(1H)-quinolinone

Using the procedure of Step D of Example 7, 6 g of the product of Step C were reacted to obtain 3.4 g of the desired product melting at 172° C.

| IR Spectrum (Nujol): | |
|---|---|
| C=O | 1638 cm$^{-1}$ |
| + | 1626 cm$^{-1}$ |
| C=C | 1610 cm$^{-1}$ |
| + | 1580 cm$^{-1}$ |
| Aromatic | 1546 cm$^{-1}$ |
| | 1520 cm$^{-1}$ |

STEP E: 4-(3-butyl-8-bromo-4-quinolinyl)-oxy]-benzyl 2 g of the product of Step D, in 100 ml of acetone were stirred at reflux with 1 ml of benzyl bromide and 2 g of potassium carbonate for 5 hours. After chromatography on silica (eluant: methylene chloride), 2.12 g of the desired product were obtained.

| IR Spectrum (CHCl$_3$): | |
|---|---|
| C=O | 1598 cm$^{-1}$ |
| + | 1554 cm$^{-1}$ |
| Aromatic | 1498 cm$^{-1}$ |

STEP F: Methyl 4'-[[3-butyl-1,4-dihydro-8-bromo-4-oxo-1-quinolinyl]-methyl](1,1'-biphenyl) 2-carboxylate A mixture of 500 mg of the product of Step E of Example 17 and 500 mg of methyl bromomethyl (1,1'-biphenyl) 2-carboxylate was maintained at 130° C. for 15 hours. After chromatography on silica (eluant: methylene chloride-methanol (95-5)), 490 mg of the desired product were obtained.

| IR Spectrum (CHCl$_3$): | |
|---|---|
| C=O | 1720 cm$^{-1}$ |
| Aromatic + | 1625 cm$^{-1}$ |
| C=C | 1614 cm$^{-1}$ |
| | 1583 cm$^{-1}$ 1540 cm$^{-1}$ |

EXAMPLE 18

4'-[(3-butyl-1,4-dihydro-8-bromo-4-oxo-1-quinolinyl)-methyl](1,1'-biphenyl) 2-carboxylic acid Using the procedure of Example 2, 380 mg of the product of Example 17 and 10 ml of N sodium hydroxide and 5 ml of ethanol were reacted to obtain 120 mg of the desired product melting at 180° C. after being crystallized from ethyl acetate.

Analysis: $C_{27}H_{24}NO_3Br$; molecular weight=490.45 Calculated: % C 66.13 % H 4.93 % N 2.86 % Br 16.29 Found: 66.4 4.9 2.8 16.2

| IR Spectrum (Nujol): | |
|---|---|
| C=O | 1706 cm$^{-1}$ |
| C=C + | 1622 cm$^{-1}$ |
| Aromatic | 1602 cm$^{-1}$ |
| | 1556 cm$^{-1}$ |
| | 1528 cm$^{-1}$ |

EXAMPLE 19

Methyl 4'-[(2-butyl-1,4-dihydro-4-oxo-1-quinolinyl)-methyl]-1,1'-biphenyl-2-carboxylate

STEP A: Ethyl 3-oxo-heptanoate 70.8 g of ethyl carbonate in solution in 50 ml of ether were added to a suspension of 27.3 g of sodium hydride (50% in oil, washed 3 times with hexane) in 250 ml of ether and the mixture was stirred for 10 minutes and 30 g of hexanone were added. The mixture was refluxed for 2 hours and then a solution of 35 ml of ether containing 12 ml of ethanol was added. The solution was cooled to 0° C. and a solution of 36 ml of acetic acid in 300 ml of water was added. 12 ml of a saturated sodium bicarbonate solution were added and extraction was carried out with ether. The extracts were washed with water, dried, filtered and evaporated to dryness under reduced pressure to obtain 100 g of an oil which was distilled under a pressure of 3 mbar at 70° C. to obtain 32.5 g of the desired product.

| NMR Spectrum CDCl₃ (250 MHz): | |
|---|---|
| CH₂—CH₃ | 0.91 ppm |
| the central central CH₂'s | 1.34–1.59 ppm |
| CH₂—C(=O)  | 2.55 ppm (t) |
| CO₂Et | 1.28 ppm (t) |
| | 4.20 ppm (q) |
| C(=O)—CH₂—C(=O) 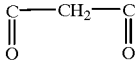 | 3.44 ppm (s) |

STEP B: Ethyl 3-(phenylamino) 2-heptenoate

A mixture of 17.9 g of aniline and 45 g of ethyl 3-oxo heptenoate of Step A was stirred for 48 hours in the presence of 5 g of activated siliporite and the reaction mixture was chromatographed on silica (eluant: hexane-ethyl acetate (95-5)) to obtain 28.7 g of the desired product.

| IR Spectrum (CHCl₃): | |
|---|---|
| NH | 3260 cm⁻¹ |
| >C=O | 1648 cm⁻¹ |
| C=C + | 1612 cm⁻¹ |
| Aromatic | 1594 cm⁻¹ |
| | 1588 cm⁻¹ |

STEP C: 2-butyl-4-(1H)-quinolinone

A solution of 28.7 g of the compound of Step B in 60 ml of diphenyl ether was heated for 45 minutes at 250° C. and the solution was allowed to cool, was impasted in 400 ml of pentane, separated and washed with pentane to obtain 16.95 g of the desired product melting at 140° C.

| IR Spectrum (CHCl₃): | |
|---|---|
| =C—NH | 3428 cm⁻¹ |
| C=O + | 1636 cm⁻¹ |
| C=C + | 1606 cm⁻¹ |
| C=N + | 1596 cm⁻¹ |
| Aromatic | 1547 cm⁻¹ |
| | 1502 cm⁻¹ |

STEP D: 4-[[(2-butyl-4-quinolinyl)-oxy]-methyl]-benzyl 3 g of the product of Step C, 2.8 ml of benzyl bromide and 4.1 g of potassium carbonate in 70 ml of acetone were stirred at reflux for 5 hours. The mixture was poured into 100 ml of water, and extraction was carried out with ethyl acetate and after chromatography on silica (eluant: methylene chloride-methanol (95-5)), 3.2 g of the desired product were obtained.

| IR Spectrum (CHCl₃): | |
|---|---|
| Absence of OH | |
| C=C + | 1620 cm⁻¹ |
| Aromatic | 1598 cm⁻¹ |
| | 1568 cm⁻¹ |
| | 1508 cm⁻¹ |

STEP E: Methyl 4'-[(2-butyl-1,4-dihydro-4-oxo-1-quinolinyl)-methyl](1,1'-biphenyl) 2-carboxylate A mixture of 1 g of 4-[(2-butyl-4-quinolinyl)-oxy]benzyl of Step D and 1.4 g of methyl bromomethyl (1,1'-biphenyl) 2-carboxylate was heated for 15 hours at 130° C. and after chromatography on silica, 1.3 g of the desired compound were obtained.

| IR Spectrum (CHCl₃): | |
|---|---|
| C=O | 1725 cm⁻¹ |
| Conjugated system + | 1623 cm⁻¹ |
| Aromatic | 1602 cm⁻¹ |
| | 1575 cm⁻¹ |
| | 1555 cm⁻¹ |

EXAMPLE 20

4'-[(2-butyl-1,4-dihydro-4-oxo-1-quinolinyl)-methyl] (1,1'-biphenyl) 2-carboxylic acid Using the procedure of Example 2, the product of Example 19 and 3 ml of N sodium hydroxide and 2 ml of ethanol were reacted to obtain after crystallization from dimethylformamide, 155 mg of the desired product melting at >260° C.

Analysis: $C_{27}H_{25}NO_3$; molecular weight=411.48 Calculated: % C 78.80 % H 6.12 % N 3.4 Found: 78.6 6.0 3.3

| IR Spectrum (Nujol): | |
|---|---|
| C=O | 1692 cm⁻¹ |
| C=O + | 1616 cm⁻¹ |
| C=C + | 1596 cm⁻¹ |
| Aromatic | 1550 cm⁻¹ |
| | 1532 cm⁻¹ |
| | 1496 cm⁻¹ |

EXAMPLE 21

Methyl 4'-[(3-butyl-1,4,5,6,7,8-hexahydro-4-oxo-1-quinolinyl)-methyl](1,1'-biphenyl-2-carboxylate (Product A) and methyl 4'-[((3-butyl-1,4,5,6,7,8-hexahydro-4-quinolinyl)-oxy]-methyl](1, 1'biphenyl)-2-carboxylate (Product B)

STEP A: 3-butyl 1,4,5,6,7,8-hexahydro-4-oxo-1-quinoline 1 g of the product of Step E of Example 1 was introduced into 60 ml of methanol and about 10 mg of platinum oxide were added. The mixture was hydrogenated under a pressure of about 200 mbar and after about 3 hours of stirring at ambient temperature, 10 mg of platinum oxide were added. The mixture was stirred for 16 hours under 200 mbar of hydrogen pressure and the solution was filtered and evaporated. After chromatography (eluant: methylene chloride-methanol 98-2), 0.6 g of the expected product melting at 223° C. were obtained.

| IR Spectrum (chloroform): | |
|---|---|
| =C—N—H | 3430 cm$^{-1}$ |
| >=O | 1632 cm$^{-1}$ |
| Conjugated systems | 1538 cm$^{-1}$ |
| | 1510 cm$^{-1}$ |

STEP B: Methyl 4'-[(3-butyl-1,4,5,6,7,8-hexahydro-4-oxo-1-quinolinyl)-methyl](1,1'-biphenyl-2-carboxylate (Product A) and methyl 4'-[((3-butyl-1,4,5,6,7,8-hexahydro-4-quinolinyl)-oxy]-methyl](1,1'biphenyl)-2-carboxylate (Product B)

0.4 g of the product of Step A were introduced into 10 ml of anhydrous acetone and 0.52 g of potassium carbonate and 0.6 g of methyl bromomethyl (1,1'-biphenyl)-2-carboxylate were added. The reaction mixture was refluxed over night and then was poured into 100 ml of water. The aqueous phase was extracted 3 times with 50 ml of ethyl acetate. The extracts were dried and evaporated to dryness. After chromatography (eluant: methylene chloride-methanol 98-2), 0.45 g of the expected product A and 0.15 g of product B were obtained.

| IR Spectrum Product A (chloroform): | |
|---|---|
| >=O | 1726 cm$^{-1}$ |
| C=C | 1637 cm$^{-1}$ |
| Aromatic | 1595 cm$^{-1}$ |
| C=O | 1547 cm$^{-1}$ |
| | 1495 cm$^{-1}$ |

| IR Spectrum Product B (chloroform): | |
|---|---|
| >=O | 1720 cm$^{-1}$ |
| Aromatic | 1617 cm$^{-1}$ |
| | 1600 cm$^{-1}$ |
| | 1589 cm$^{-1}$ |
| | 1519 cm$^{-1}$ |
| | 1482 cm$^{-1}$ |

EXAMPLE 22

4'-[(3-butyl-1,4,5,6,7,8-hexahydro-4-oxo-1-quinolinyl)-methyl](1,1'-biphenyl)-2-carboxylic acid 0.43 g of product A of Example 21 were introduced into 10 ml of a normal sodium hydroxide solution and the mixture was heated for one hour at 60° C., stirred for about one hour and 1 ml of ethanol was added. The mixture was stirred for one night at about 40° C., followed by cooling to ambient temperature and slowly adding glacial acetic acid until the acid crystallized. The mixture was stirred for about one hour, followed by separating, washing with water and then with ether. Crystallization was carried out from 80 ml of ethanol to obtain 0.310 g of the expected product melting at 260° C.

| IR Spectrum (Nujol): | |
|---|---|
| >=O | 1672 cm$^{-1}$ |
| Conjugated system | |
| C=O | 1630 cm$^{-1}$ |
| C=C | 1600 cm$^{-1}$ |
| Aromatic | 1535 cm$^{-1}$ |
| | 1520 cm$^{-1}$ |

Starting with product B of Example 21 and proceeding with the same conditions, 4'-[((3-butyl-1,4,5,6,7,8-hexahydro-4-oxo-1-quinolinyl)-oxy)-methyl](1,1'-biphenyl)-2-carboxylic acid was obtained.

EXAMPLE 23

Methyl 4'-[(3-butyl-1,4,5,6,7,8-hexahydro-6-methyl-4-oxo-1-quinolinyl)-methyl](1,1'-biphenyl)-2-carboxylate (product A) and methyl 4'-[((butyl-1,4,5,6,7,8-hexahydro-6-methyl-4-quinolinyl)-oxy)-methyl](1,1'-biphenyl)-2-carboxylate (product B)

STEP A: 2-ethyl-6-methyl-3-butyl-4-hydroxy-2,6-quinoline-dicarboxylate a) Diethyl 2-butyl-3-[(4-(methoxycarbonyl)-phenyl)-amino]-2-butenedioate 27.8 g of methyl 4-aminobenzoate and 47 g of diethyl 2-butyl-3-oxo-butanedioate were mixed and 2 g of activated siliporite were added. The mixture was stirred for about 30 hours at 60° C. and after chromatography (eluant: hexane-ethyl acetate 95-5), 70 g of the expected product were obtained.

b) 2-ethyl-6-methyl-3-butyl-4-hydroxy-2,6-quinoline dicarboxylate

The 70 g of product of a) were mixed with 70 ml of DOWTHERM and the mixture was heated at about 250° C. for 30 minutes, cooled down, impasted in ether and separated to obtain 45 g of the expected product melting at 160° C.

| IR Spectrum (chloroform): | |
|---|---|
| =C—NH— | 3422 cm$^{-1}$ |
| | 3380 cm$^{-1}$ |
| >=O | 1742 cm$^{-1}$ |
| | 1715 cm$^{-1}$ |
| | 1631 cm$^{-1}$ |
| Aromatic | 1603 cm$^{-1}$ |
| C=C | 1577 cm$^{-1}$ |
| | 1525 cm$^{-1}$ |

STEP B: 3-butyl-4-hydroxy-6-quinoline carboxylic acid a) 3-butyl-1,4-dihydro-4-hydroxy-2,6-quinoline dicarboxylic acid 40 g of the product of Step A were introduced into 150 ml of concentrated sodium hydroxide and 15 ml of ethanol were added. The mixture was heated for about 4 hours at about 80° C. and after 100 ml of an ice and water mixture were added, the mixture was acidified with concentrated hydrochloric acid, separated, washed with water and dried to obtain 24 g of the expected product melting at >260° C.

b) 3-butyl-4-hydroxy-6-quinoline carboxylic acid 24 g of the product of a) were introduced into 350 ml of DOWTHERM and the mixture was heated at about 250° C. for 5 hours, cooled to ambient temperature, impasted in ether and separated. The residue was washed with water and dried to obtain 17.8 g of the expected product melting at >260° C.

| IR Spectrum (Nujol): | |
|---|---|
| >=O | 1702 cm$^{-1}$ |
| | 1662 cm$^{-1}$ |
| | 1640 cm$^{-1}$ |
| C=C | 1616 cm$^{-1}$ |
| Aromatic | 1597 cm$^{-1}$ |
| | 1568 cm$^{-1}$ |
| | 1492 cm$^{-1}$ |

STEP C: 3-butyl-6-hydroxymethyl-4-(1H)-quinoline 3 g of the product of Step B were introduced into 800 ml of tetrahydrofuran and 1.8 g of lithium aluminum tetrahydride was added followed by stirring for about 5 hours at ambient temperature. About 5 ml of a tetrahydrofuran-water solution 80-20 were added and a saturated solution of double tartrate salt was added slowly. Filtration was carried out and the precipitate was washed with tetrahydrofuran and dried to obtain 2.5 g of the expected product melting at >260° C.

| IR Spectrum (Nujol): | |
|---|---|
| C=O | 1638 cm$^{-1}$ |
| Conjugated system | 1620 cm$^{-1}$ |
| Aromatic | 1568 cm$^{-1}$ |
| | 1550 cm$^{-1}$ |
| | 1508 cm$^{-1}$ |
| | 1490 cm$^{-1}$ |

STEP D: 3-butyl-1,4,5,6,7,8-hexahydro-6-methyl-4-(1H)-quinoline (1) (as well as 3-butyl-1,4,5,6,7,8-hexahydro-6-hydroxymethyl-4-(1H)-quinoline (2))

0.5 g of the product of Step C in 100 ml of methanol was admixed with 10 mg of platinum oxide and the mixture was hydrogenated under about 300 mbar for about 24 hours. Filtration was carried out and the filtrate was washed with methanol and dried. After chromatography (eluant: methylene chloride-methanol 95-5), 0.47 g of the expected product melting at approx. 260° C. was obtained.

| IR Spectrum (Nujol (1)): | |
|---|---|
| >=O | 1632 cm$^{-1}$ |
| Conjugated system | 1603 cm$^{-1}$ |
| C=N | 1500 cm$^{-1}$ |
| C—N | |

STEP E: Methyl 4'-[(3-butyl-1,4,5,6,7,8-hexahydro-6-methyl-4-oxo-1-quinolinyl)-methyl](1,1'-biphenyl)-2-carboxylate (product A) and methyl 4'-[((butyl-1,4,5,6,7,8-hexahydro-6-methyl-4-quinolinyl)-oxy)-methyl](1,1'-biphenyl)-2-carboxylate (product B)

Using the procedure of Example 21, 0.45 g of the product A of Step D of Example 23 in 20 ml of anhydrous acetone, 0.55 g of potassium carbonate and 0.61 g of methyl bromomethyl (1,1'-biphenyl)-2-carboxylate were added. The reaction medium was heated at reflux for 3 hours and poured into 100 ml of water. The aqueous phase was extracted 3 times with 50 ml of ethyl acetate. The organic phase was dried and evaporated. After chromatography (eluant: methylene chloride-methanol 95-5), 0.58 g of the expected product and 0.1 g of product B were obtained.

| IR Spectrum (chloroform Product A): | |
|---|---|
| —C—OCH$_3$ ‖ O | 1725 cm$^{-1}$ |
| | 1434 cm$^{-1}$ |
| C=O | 1638 cm$^{-1}$ |
| C=C | 1600 cm$^{-1}$ |
| Aromatic | 1545 cm$^{-1}$ |
| | 1494 cm$^{-1}$ |

EXAMPLE 24

4'-[(3-butyl-1,4,5,6,7,8-hexahydro-6-methyl-4-oxo-1-quinolinyl)-methyl](1,1'-biphenyl)-2-carboxylic acid Using the procedure of Example 22, 0.4 g of the product A of example 23 in 10 ml of 2N sodium hydroxide was stirred over night at about 60° C. The mixture was cooled to ambient temperature, acidified with glacial acetic acid, decanted, impasted in a 2N hydrochloric acid solution, followed by separating, drying and crystallizing from 50 ml of an ethanol-water mixture (49-1) to obtain 0.220 g of the expected product melting at 255° C.

| IR Spectrum (Nujol): | |
|---|---|
| >=O | 1675 cm$^{-1}$ |
| | 1628 cm$^{-1}$ |
| C=C | 1600 cm$^{-1}$ |
| Aromatic | 1533 cm$^{-1}$ |
| | 1517 cm$^{-1}$ |

Starting with product B of Example 23, and proceeding under the same conditions, 4'-[[(3-butyl-1,4,5,6,7,8-hexahydro-6-methyl-4-quinolinyl)-oxy]-methyl](1,1'-biphenyl)-2-carboxylic acid was obtained.

Starting with product (2) of Step D of Example 23 and proceeding in the same manner, (product A1) methyl 4'-[(3-butyl-1,4,5,6,7,8-hexahydro-6-hydroxymethyl-4-oxo-1-quinolinyl)-methyl](1,1'-biphenyl)-2-carboxylate and (product B1) methyl 4-[[(3-butyl-1,4,5,6,7,8-hexahydro-6-hydroxymethyl-4-quinolinyl)-oxy]-methyl](1,1'-biphenyl)-2-carboxylate were obtained.

Starting with products A1 and B1 above and proceeding in the same manner as in Example 24, 4'-[(3-butyl-1,4,5,6,7,8-hexahydro-6-hydroxymethyl-4-oxo-1-quinolinyl)-methyl](1,1'-biphenyl)-2-carboxylic acid and 4'-[[(3-butyl-1,4,5,6,7,8-hexahydro-6-hydroxy-methyl-4-quinolinyl)-oxy]-methyl](1,1'-biphenyl)-2-carboxylic acid were obtained from A1 and B1, respectively.

The products of Examples 25 to 72 which follow correspond to formula $I_B$ as defined above in which X is oxygen, $R_1$ is n-butyl, $R_5$—Y is

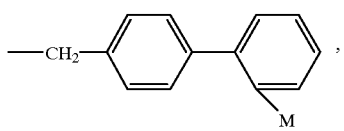

and $R_2$, $R_3$, $R_4$ as well as M have the meanings indicated in the table hereafter.

| Ex. | $R_2$ | $R_3$ | $R_4$ | M |
|---|---|---|---|---|
| 25 | 6-COOCH$_3$ | H | H | CO$_2$CH$_3$ |
| 26 | 6-COOH | " | " | COOH |
| 27 | 6-CH$_2$OH | " | " | CO$_2$CH$_3$ |
| 28 | " | " | " | COOH |
| 29 | H | 8-COOCH$_3$ | " | CO$_2$CH$_3$ |
| 30 | " | 8-COOH | " | COOH |
| 31 | " | " | H | COOEt | CO$_2$CH$_3$ |
| 32 | " | " | COOH | COOH |
| 33 | 6-CON | " | " | CO$_2$CH$_3$ |
| 34 | " | " | " | COOH |
| 35 | H | 7-CHO | " | CO$_2$CH$_3$ |
| 36 | " | " | " | COOH |
| 37 | " | 7(CH$_2$)$_2$COOCH$_3$ | " | CO$_2$CH$_3$ |
| 38 | " | 7(CH$_2$)$_2$COOH | " | COOH |
| 39 | 6 COOCH$_3$ | H | " | CO$_2$CH$_3$ |
| 40 | 6 COOH | " | " | COOH |
| 41 | 6-CHO | " | " | CO$_2$CH$_3$ |
| 42 | " | " | " | COOH |
| 43 | 6-(CH$_2$)$_2$—Ph | " | " | CO$_2$CH$_3$ |
| 44 | " | " | " | COOH |
| 45 | H | 7 COOCH$_3$ | " | CO$_2$CH$_3$ |
| 46 | " | 7 COOH | " | COOH |
| 47 | " | 8-CF$_3$ | " | CO$_2$CH$_3$ |
| 48 | " | " | " | COOH |
| 49 | " | 7-CH$_2$—COOCH$_3$ | " | CO$_2$CH$_3$ |
| 50 | " | 7-CH$_2$—COOH | " | COOH |
| 51 | " | 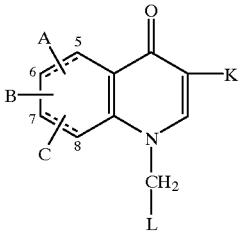 | " | 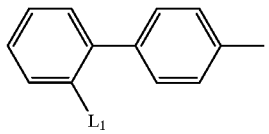 |
| 52 | " | " | " | |

The products of Examples 25 to 52 have been prepared as indicated for the products of the Examples described above. The products of Examples 26, 28, 30, 32, 34, 36, 38, 40, 42, 44, 46, 48, 50 and 52 are characterized in the table hereafter by their melting points and their chemical microanalysis results.

| | | Microanalysis | | | | | |
|---|---|---|---|---|---|---|---|
| | | Calculated | | | Found | | |
| Ex. | M.p. | C % | H % | N % | C % | H % | N % |
| 26 | >260° C. | 73.83 | 5.53 | 3.07 | 73.1 | 5.4 | 3.0 |
| 28 | 258° C. | 76.17 | 6.16 | 3.14 | 76.1 | 6.2 | 3.1 |
| 30 | 219° C. | 73.83 | 5.53 | 3.07 | 73.7 | 5.2 | 2.9 |
| 32 | 248° C. | 73.83 | 5.53 | 3.07 | 73.9 | 5.5 | 3.1 |
| 34 | 150° C. | 75.57 | 6.3 | 5.5 | 75.7 | 6.2 | 5.4 |
| 36 | 225° C. | 76.51 | 5.73 | 3.18 | 76.7 | 5.7 | 3.0 |
| 38 | 210° C. | 74.52 | 6.04 | 2.90 | 74.4 | 5.9 | 2.9 |
| 40 | >260° C. | 74.83 | 5.65 | 2.9 | 74.6 | 5.6 | 2.7 |
| 42 | >260° C. | 76.5 | 5.73 | 3.18 | 76.1 | 5.8 | 3 |
| 44 | 250° C. | 81.5 | 6.45 | 2.72 | 81.2 | 6.4 | 2.6 |
| 46 | >260° C. | 74.83 | 5.65 | 2.91 | 74.6 | 5.9 | 3.1 |
| 48 | 196° C. | 70.14 | 5.04 | | 70.2 | 5.1 | |
| 50 | 245° C. | 74.18 | 5.80 | 2.98 | 74.0 | 5.9 | 2.9 |
| 52 | dec. 190–195° C. | 72.16 | 6.05 | 15.78 | 71.9 | 6.1 | 15.1 |

The products described in the table below which constitute Examples 53 to 128 correspond to the formula:

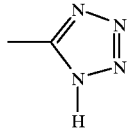

in which A, B and C have the meanings and the position on the ring (that is positions 5, 6, 7 or 8) indicated in the table L is the numbers 1, 2, 3, 4, 5, 6, 7 or 8 which have the following meanings:

Numbers 1 to 6 are biphenyl of the formula such that

Number 1 corresponds to L1 being —CH═CH—CO$_2$CH$_3$

Number 2 corresponds to L1 being —CH═CH—CO$_2$H

Number 3 corresponds to L1 being —CO$_2$CH$_3$

Number 4 corresponds to L1 being —CO$_2$H

Number 5 corresponds to L1 being tetrazolyl salified by triphenyl methyl

Number 6 corresponds to L1 being tetrazolyl

Number 7 corresponds to L1 being —SO$_2$—NH—CO—NH—CH$_2$—CH═CH$_2$

Numbers 8 and 9 are phenyl of the formula

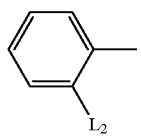

such that

Number 8 corresponds to L2 being —CH$_2$—CO$_2$CH$_3$
Number 9 corresponds to L2 being —CH$_2$—CO$_2$H
K has the meaning indicated in the table below

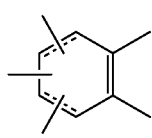

is either

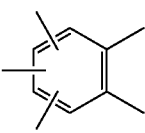

indicated by Q in the column headed "N", or

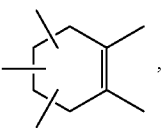

indicated by TQ in the column headed "N".

The products were obtained by the processes indicated above and 0° C. is the melting point of the products

| No Ex | A | B | C | K | L | N | M.p. ° C. |
|---|---|---|---|---|---|---|---|
| 53 | H | pyrrolidinyl  7-CH$_2$—N⟨pyrrolidine⟩ | H | nBu | (3) | Q | |
| 54 | " | pyrrolidinyl  7-CH$_2$—N⟨pyrrolidine⟩ | " | " | (4) | " | |
| 55 | " | H | " | " | (8) | " | |
| 56 | " | " | " | " | (9) | " | 166 |
| 57 | 6-CH$_3$ | H | " | " | (3) | " | |
| 58 | " | " | " | " | (4) | " | ≃215 |
| 59 | H | H | " | " | (5) | TQ | |
| 60 | " | " | " | " | (6) | " | >260 |
| 61 | 6-C(=O)—N⟨pyrrolidine⟩ | " | " | " | (3) | " | |
| 62 | " | " | " | " | (4) | " | 191 |
| 63 | H | 7-CO$_2$CH$_3$ | " | " | (3) | " | |
| 64 | " | 7-CO$_2$H | " | " | (4) | " | 236 |
| 65 | 6-CH$_2$—S—C$_6$H$_5$ | H | " | " | (3) | Q | |
| 66 | " | " | " | " | (4) | " | 210 |
| 67 | H | " | " | " | (1) | " | |
| 68 | " | " | " | " | (2) | " | 140 dec. |
| 69 | " | 8-CH$_3$ | " | " | (3) | " | |
| 70 | " | " | " | " | (4) | " | ≃201 |
| 71 | 6-CH$_2$—O—C$_2$H$_5$ | H | " | " | (3) | " | |
| 72 | " | " | " | " | (4) | " | 175 |
| 73 | H | 7-CH$_2$—N⟨pyrrolidine⟩ | H | nBu | (3) | Q | |
| 74 | " | " | " | " | (4) | " | 205 |
| 75 | H | 8-CO$_2$CH$_3$ | " | " | (5) | " | |
| 76 | " | " | " | " | (6) | " | 217 |

-continued

| No Ex | A | B | C | K | L | N | M.p. °C. |
|---|---|---|---|---|---|---|---|
| 77 | " | 8-CO₂H | " | " | (5) | " | |
| 78 | " | " | " | " | (6) | " | 252 |
| 79 | 6-CH=CH—C₆H₅ (Z) | H | " | " | (3) | " | |
| 80 | 6-CH=CH—C₆H₅ (Z) | " | " | " | (4) | " | 212 |
| 81 | H | " | " | " | (5) | " | |
| 82 | " | " | " | " | (6) | " | 255 |
| 83 | 5-CH₃ | 7-CH₃ | " | " | (5) | " | |
| 84 | " | " | " | " | (6) | " | 158 |
| 85 | H | 7-CO₂CH₃ | " | " | (5) | " | |
| 86 | " | " | " | " | (6) | " | |
| 87 | " | 7-CO₂H | " | " | (5) | " | |
| 88 | " | " | " | " | (6) | " | 190 |
| 89 | " | 8-CO₂CH₃ | " | CH₃ | (5) | " | |
| 90 | " | 8-CO₂H | " | " | (6) | " | |
| 91 | " | 8-CO₂H | " | " | (5) | " | |
| 92 | " | " | " | " | (6) | " | >260 |
| 93 | H | 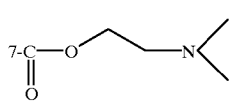 | H | nBu | (5) | Q | |
| 94 | " | " | " | " | (6) | " | 190 |
| 95 | 6-CH₂— pyridine | H | " | " | (5) | " | |
| 96 | " | " | " | " | (6) | " | 182 |
| 97 | " | 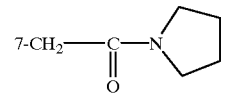 | " | " | (3) | " | |
| 98 | " | " | " | " | (4) | " | 160 |
| 99 | " | 8-CO₂CH₃ | " | C₂H₅ | (5) | " | |
| 100 | " | " | " | " | (6) | " | |
| 101 | " | 8-CO₂H | " | " | (5) | " | |
| 102 | " | " | " | " | (6) | " | >260 |
| 103 | 6-CH=CH—C₆H₅ (E) | H | " | nBu | (3) | " | |
| 104 | 6-CH=CH—C₆H₅ (E) | " | " | " | (4) | " | 244 |
| 105 | 6-CH₂—S—C₆H₅ | " | " | " | (5) | " | |
| 106 | " | " | " | " | (6) | " | >260 |
| 107 | 6-CH₂—S(O)—C₆H₅ | " | " | " | (5) | " | |
| 108 | " | " | " | " | (6) | " | >260 |
| 109 | 6-CH₂—S(O)(O)—C₆H₅ | " | " | " | (5) | " | |
| 110 | " | " | " | " | (6) | " | |
| 111 | 6-CH₂—S—CH₃ | H | H | nBu | (5) | Q | |
| 112 | " | " | " | " | (6) | " | 210 |
| 113 | 6-F | 7-F | 8F | " | (5) | " | |
| 114 | " | " | " | " | (6) | " | 243 |
| 115 | 6-F |  | " | " | (5) | " | |

-continued

| No Ex | A | B | C | K | L | N | M.p. °C. |
|---|---|---|---|---|---|---|---|
| 116 | " | " | " | " | (6) | " | 203 |
| 117 | H | 8-CO$_2$CH$_3$ | H | H | (7) | " | |
| 118 | " | 8-CO$_2$H | " | " | (7) | " | |
| 119 | " | 8-CO$_2$CH$_3$ | " | CO$_2$CH$_3$ | (5) | " | |
| 120 | " | 8-CO$_2$H | " | CO$_2$H | (6) | " | |
| 121 | " | 8-CO$_2$CH$_3$ | " | nPr | (5) | TQ | |
| 122 | " | 8-COOH | " | " | (6) | " | |
| 123 | " | 8-CO$_2$CH$_3$ | " | C$_2$H$_5$ | (7) | Q | |
| 124 | " | 8-CO$_2$H | " | " | (7) | " | |
| 125 | " | 8-CO$_2$CH$_3$ | " | cyclopropyl | (5) | " | |
| 126 | " | 8-CO$_2$H | " | " | (6) | " | |
| 127 | " | H | " | nPr | (5) | " | |
| 128 | " | " | " | " | (6) | " | |

Among the products of formula $I_D$ as defined above, there can be mentioned particularly the products described below which can be obtained as Examples 129 to 146:

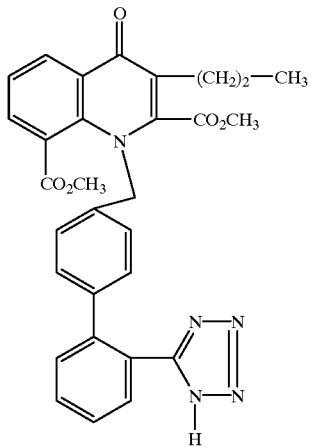

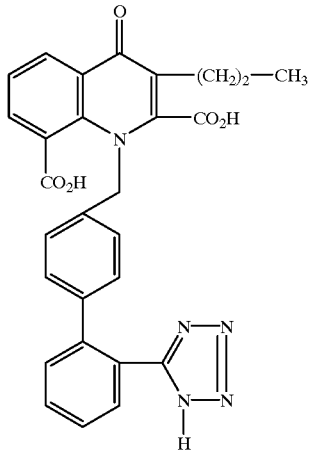

-continued

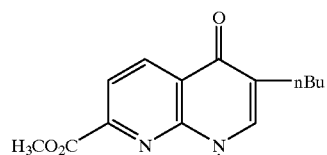

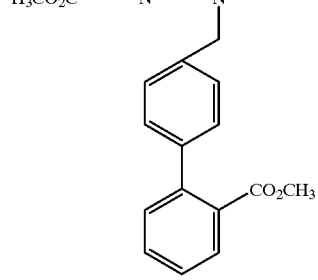

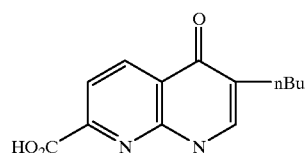

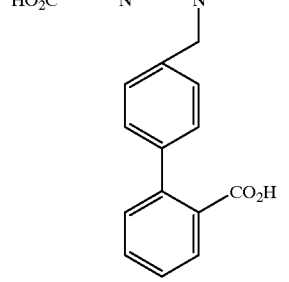

65
-continued
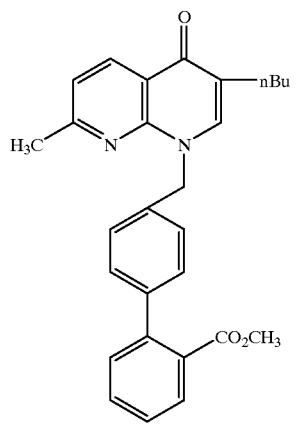
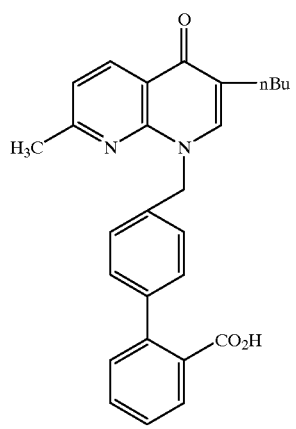
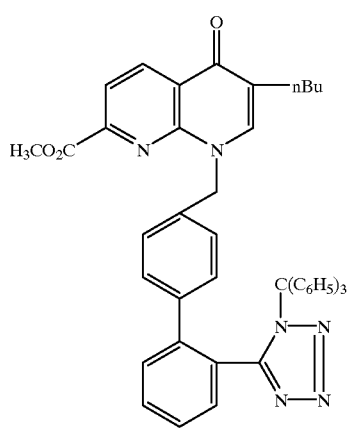
66
-continued
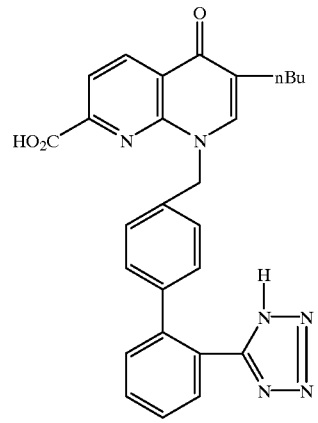
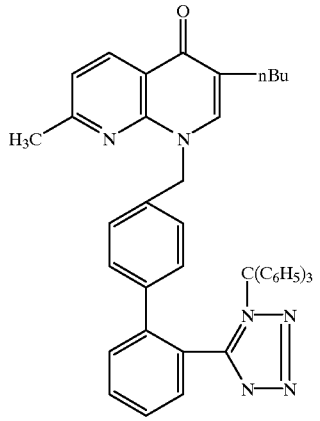
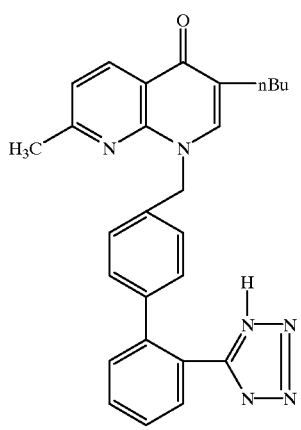

Similar to the products of Examples 131 to 138 above, in which the nitrogen atom in position 8 is situated in position 7 of the quinolone while the substituent in position 7 is situated in position 8, can be obtained according to the process described above and constitute Examples 139 to 146.

EXAMPLE 147
Pharmaceutical Composition

Tablets were prepared corresponding to the following formula 10 mg of the Product of Example 10 and sufficient excipient of lactose, talc, starch, magnesium stearate for a tablet weighing 100 mg.

Pharmacological Results

1) Test on the Angiotensin II Receptor

A fresh membrane preparation obtained from the liver of a rat was used and the tissue was ground up in a polytron in a Tris 50 mM pH 7.4 buffer. After being ground up, the tissue was centrifuged 3 times at 30,000 g for 15 minutes with intermediate taking up of the deposits in the Tris pH 7.4 buffer. The last deposits were suspended in a pH 7.4 incubation buffer (Tris 20 mM, NaCl 135 mM, KCl 10 mM, glucose 5 mM, $MgCl_2$ 10 mM, phenyl methyl sulfonyl fluoride 0.3 mM, bacitracine 0.1 mM (0.2% bovine albumin serum). 2 ml aliquoted fractions were divided into hemolysis tubes and $^{125}I$ angiotensin II (25,000 DPM/tube) and the product to be studied were added. The product has first tested at $3 \times 10^{-5}M$ in triplicate. When the test product displaced more than 50% of the radioactivity linked specifically to the receptor, it was tested again according to a range of 7 concentrations to determine the concentration that inhibited the radioactivity linked specifically to the receptor by 50%. In this way, the 50% inhibiting concentration was determined.

The non-specific bond was determined by the addition of the product of Example 94 of the European Patent No. 0,253,310 at $10^{-5}M$ (in triplicate). The deposit was incubated at 25° C. for 150 minutes, put back in a water bath at 0° C. for 5 minutes, filtered under vacuum, rinsed with Tris pH 7.4 buffer and the radioactivity was counted in the presence of scintillating Triton. The results were expressed directly as a 50% inhibiting concentration ($IC_{50}$), that is to say as a concentration of product studied, expressed in nM, necessary to displace 50% of the specific radioactivity fixed on the receptor studied. The results are in the following Table.

| Product of example | $IC_{50}$ in nanomoles |
| --- | --- |
| 10 | 92 |
| 4 | 180 |
| 6 | 400 |
| 16 | 79 |
| 18 | 74 |
| 22 | 90 |
| 30 | 54 |
| 52 | 8.7 |

2) Revealing the Antagonistic Activity of Angiotensin II on the Isolated Portal Vein The portal vein was removed from male Wistar rats weighing about 350 g (IFFA Credo France) after cervical dislocation, and put rapidly into a physiological solution (see below) at ambient temperature. A ring of about 1 mm was mounted in a bath with an isolated element containing 20 ml of the following physiological solution (composition in mM: NaCl 118.3-KCl 4.7-$MgSO_4$ 1.2-$KH_2PO_4$ 1.2-$NaHCO_3$ 25-glucose 11.1-$CaCl_2$ 2.5). The medium was maintained at 37° C. and oxygenated with a mixture of $O_2$ 95%, $CO_2$ 5%. The initial pressure imposed was 1 g and the rings were left at rest for 60 to 90 minutes. To avoid spontaneous contractions, verapamil was added to the incubation bath ($1.10^{-6}M$). At the end of the rest period, angiotensin II (Ciba hypertensis) $3.10^{-8}M$ were added to the incubation bath and left in contact with the preparation for one minute. This operation was repeated every 30 minutes with the tissue being washed 3 or 4 times between two stimulations with angiotensin. The compound to be studied was introduced into the bath 15 minutes before a new stimulation with angiotensin. As increasing concentrations of the molecule were used, an $IC_{50}$ (concentration that produced a 50% inhibition of the response to angiotensin) was calculated, expressed in nanomoles.

| Product of example | $IC_{50}$ in nanomoles |
| --- | --- |
| 10 | 31 |
| 4 | 96.5 |
| 6 | 66 |
| 12 | 49 |
| 16 | 31.7 |

3) Test for Antagonistic Activity of Angiotensin II on a Demedullated Rat

Male Sprague-Dawley rats weighing 250 to 350 g were anaesthetized by an intraperitoneal injection of sodium pentobarbital (60 mg/kg). The diastolic arterial pressure was recorded using a heparinated catheter (PE50) introduced into the left carotid of the animal, and connected to a pressure calculator (Gould, Pressure Processor) by a Gould pressure sensor. A catheter was introduced into the right jugular vein of the animal for the injection of the molecules to be studied. The animal was placed under assisted respiration and a bilateral section of the pneumogastric nerves was carried out. The rat was then demedullated. After a sufficient period of stabilization, the study of the antagonism of the compounds vis-a-vis angiotensin II (Ciba Hypertensin) was carried out in the following manner.

1—Three consecutive injections of angiotensin II (0.75 micrograms/kg) spaced out over 15 minutes allowed a reproducible and stable pressure response to be obtained.

2—While keeping a time period of 15 minutes for the administration of angiotensin II, the molecules to be studied were injected 5 minutes before angiotensin II.

The pressure effects of angiotensin II in the presence of the antagonist were expressed as a percentage of the pressure effects of angiotensin II administered on its own. The 50% inhibiting dose of the effect studied was determined. Each animal was considered as its own control and the results are in the following Table

| Product of example | 50% inhibiting dose (mg/kg) |
|---|---|
| 10 | 1.27 |
| 4 | 7.55 |
| 6 | 6.65 |
| 12 | 3.76 |
| 16 | 1.2 |
| 18 | 3.9 |
| 50 | 0.61 |
| 52 | 0.23 |
| 22 | 1 |
| 30 | 0.21 |

4) Passive Avoidance Test

Male mice (CD$_1$ Charles River) weighing 25–30 g were placed in the illuminated part of a box with two compartments communicating by an opening (F. Barzaghi and G. Giuliani, Brit. J. Pharmacol. undergoing publication). When the mouse passed from the illuminated compartment to the darkened compartment, the opening closed and the mouse was immediately punished by an electric shock to the paws. The animal subjected to this procedure learned to memorize the punishment. Indeed, if it was put back in the illuminated compartment, it would avoid crossing the opening and re-entering the darkened compartment. To bring about amnesia, the animals were treated with SCOPOLAMINE (0.7 mg/kg I.P.) 15 minutes before the learning process and the products were administered orally at doses of 0.1; 0.25; 1; 2.5; 10; 25; 100; 250; 1000 ug/kg using 10 to 50 animals per dose.

The anti-amnesic effect of the products was evaluated 24 hours after treatment, using the same protocol as that used for the learning process. The time taken by the animal to return to the darkened room (time limit 180 seconds) was used as the evaluation parameter. Under the same experimental conditions, control animals entered with a time lapse of 40–50 seconds. The active products were those that brought about a significant increase in the latency time with a dose-response curve in the shape of a bell. The results were expressed as percentages of increase in the latency time, relative to the corresponding controls and the following results were obtained:

| | PERCENTAGE OF INCREASE IN THE LATENCY TIME RELATIVE TO THE CONTROLS Dose: µg/kg, s.c. | | | | | | | | |
|---|---|---|---|---|---|---|---|---|---|
| EX. | 0.1 | 0.25 | 1 | 2.5 | 10 | 25 | 100 | 250 | 1000 |
| 22 | | | | | 8 (20) | 26 (20) | 66 (20) | 128 (20) | 127 (20) |
| 30 | | | 23 (20) | | 37 (20) | 65 (30) | 91 (30) | 144 (20) | 126 (20) |
| 38 | 1 (10) | | 57 (10) | | 118 (30) | 132 (20) | 131 (20) | 101 (10) | 158 (10) |
| 56 | | | | | 24 (20) | 49 (20) | 98 (20) | 105 (20) | 122 (20) |
| 50 | 20 (20) | 31 (20) | 84 (30) | 93 (20) | 190 (20) | 225 (20) | 149 (20) | | |
| 58 | 3 (20) | | 29 (20) | | 112 (30) | 110 (20) | 129 (20) | | |

Various modifications of the products and methods of the invention may be made without departing from the spirit or scope thereof and it should be understood that the invention is intended to be limited only as defined in the appended claims.

What we claim is:

1. A compound of the formula

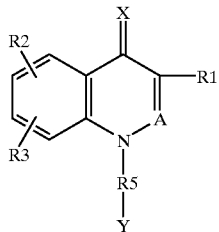

wherein $R^1$ is selected from the group consisting of hydrogen, alkyl, alkenyl and alkynyl, each of up to 6 carbon atoms, acyl of up to 6 carbon atoms and —CN, $R_2$ and $R_3$ are individually selected from the group consisting of a) hydrogen, halogen, —OH, pyrrolidinyl, pyrrolidinylcarbonyl, —SH, —CN, —NO$_2$, sulfo and acyl of a carboxylic acid of up to 12 carbon atoms, tetrazolyl, tetrazolyl salified with a alkali metal, cycloalkyl of 3 to 7 carbon atoms, free carboxy, carboxy salified with an alkali metal and carboxy esterified with alkyl of 1 to 4 carbon atoms, b) alkyl, alkenyl, alkylthio and alkoxy, each of up to 6 carbon atoms and unsubstituted or substituted by hydroxyl, alkoxy, free carboxy, carboxy salified with an alkali metal and esterified carboxy, phenyl, pyrrolidinyl, pyrrolidinylcarbonyl, pyridylthio and phenylthio with —S— optionally oxidized to SO and SO$_2$ and alkylthio of 1 to 6 carbon atoms, c) phenyl, phenylalkyl, phenylalkenyl, phenoxy and phenylthio with up to 6 alkyl or alkenyl carbon atoms

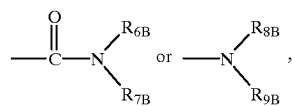

$R_{6B}$ and $R_{7B}$ or $R_{8B}$ and $R_{9B}$ are individually selected from the group consisting of hydrogen, alkyl of 1 to 6 carbon atoms and alkyl of up to 6 carbon atoms unsubstituted or substituted with a hydroxy, halogen, alkyl or alkenyl of up to 6 carbon atoms substituted with alkoxy of 1 to 6 carbon atoms, phenyl or phenylalkyl of 1 to 6 alkyl carbon atoms and the phenyl moiety being unsubstituted or substituted with a member of the group consisting of a') halogen, —OH, —CN, —CF$_3$, —NO$_2$, b') alkyl, alkenyl, alkoxy, alkylthio and acyl of a carboxylic acid, each of up to 6 carbon atoms and free carboxy, carboxy salified with a pharmaceutically acceptable salt and alkyl esterified carboxy, $R_{8B}$ and $R_{9B}$ individually or one of $R_{6B}$ or $R_{7B}$ is acyl of a carboxylic acid up to 6 carbon atoms, X is oxygen or sulfur, A is —CR$_4$—, R$_4$ has the value of R$_1$ or free carboxy, carboxy salified with an alkali metal and carboxy esterified with alkyl of 1 to 4 carbon atoms with the proviso R$_1$ is not hydrogen when A is —CH—, R$_5$ is a divalent alkylene of 1 to 4 carbon atoms, Y is Y$_{1B}$—B—Y$_{2B}$, Y$_{1B}$ is phenyl unsubstituted or substituted by one of the values of R$_{2B}$ or R$_{3B}$, B is selected from the group consisting of a single bond,

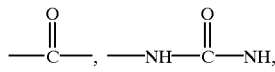

—O—(CH$_2$)$_n$— and —S—(CH$_2$)$_n$, n is an integer from 0 to 4, if B is a single bond, Y$_{2B}$ is selected from the group consisting of hydrogen, halogen, —OH, —CN, —NO$_2$, —CF$_3$, tetrazole, isoxazole, phenyl unsubstituted or substituted with one of the values of R$_{2B}$ or R$_{3B}$ and free, salified or esterified carboxy or if B is other than a single bond, Y$_{2B}$ has the value of Y$_{1B}$ except the compounds wherein X is oxygen and either A is —CH— substituted by methyl unsubstituted or substituted with free or esterified carboxy and R$_1$, R$_{2B}$ and R$_{3B}$ are hydrogen and —R$_5$—Y$_B$ is fluorobenzyl or A is —CH— R$_1$, R$_{2B}$ are methyl and —R$_5$—Y$_B$ is benzyl.

2. A compound of the formula

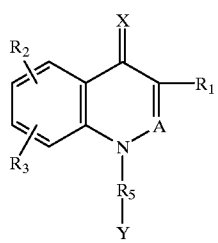

(I)

wherein R$_1$ is selected from the group consisting of hydrogen, alkyl, alkenyl and alkynyl of up to 6 carbon atoms and —CN, R$_2$ and R$_3$ are individually a) hydrogen, halogen, —OH, —SH, —CN, —NO$_2$, sulfo, benzoyl, acyl of a carboxylic acid of up to 12 carbon atoms, cycloalkyl of 3 to 7 carbon atoms, b) alkyl, alkenyl, alkynyl, alkoxy and alkylthio, each of up to 6 carbon atoms, c) phenyl, phenylalkyl, phenylalkenyl, phenoxy and phenylthio with up to 6 alkyl or alkenyl carbon atoms

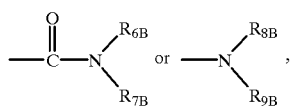

either R$_6$ and R$_7$ or R$_8$ and R$_9$ are individually selected from the group consisting of hydrogen, alkyl and alkenyl of up to 6 carbon atoms unsubstituted or substituted with halogen or —OH, alkyl and alkenyl of 2 to 6 carbon atoms substituted by alkoxy of 1 to 6 carbon atoms, phenyl and phenylalkyl of 1 to 6 carbon atoms unsubstituted or substituted with a member of the group consisting of halogen, —OH, —CN, —CF$_3$, —NO$_2$, alkyl, alkoxy, alkylthio and acyl of a carbocyclic acid of up to 6 carbon atoms and free carboxy, carboxy salified with a non-toxic pharmaceutically acceptable base and esterified carboxy with 1 to 4 alkyl carbon atoms or R$_8$ and R$_9$ individually and one of R$_6$ or R$_7$ is acyl of a carboxylic acid of up to 6 carbon atoms, X is oxygen or sulfur, A is —CR$_4$—, R$_4$ has the value of R$_1$ with the proviso that R$_1$ is not hydrogen when A is —CH—, R$_5$ is alkylene of 1 to 4 carbon atoms, Y is —Y$_1$—B—Y$_2$, Y$_1$ is phenyl unsubstituted or substituted by R$_2$ or R$_3$, B is selected from the group consisting of a single bond,

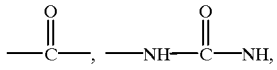

—O—(CH$_2$)$_n$— and —S—(CH$_2$)$_n$, n is an integer from 0 to 4, when B is a single bond, Y$_2$ is selected from the group consisting of hydrogen, halogen, —OH, —CN, —NO$_2$, —CF$_3$, tetrazole, isoxazole, phenyl unsubstituted or substituted by R$_2$ or R$_3$ and free carboxy, carboxy salified with a non-toxic, pharmaceutically acceptable base and esterified carboxy except the compounds wherein X is oxygen and either A is CH substituted by methyl unsubstituted or substituted by free or esterified carboxy, R$_1$, R$_2$ and R$_3$ are hydrogen and —R$_5$—Y$_B$ is benzyl.

3. A compound of claim 1 of the formula

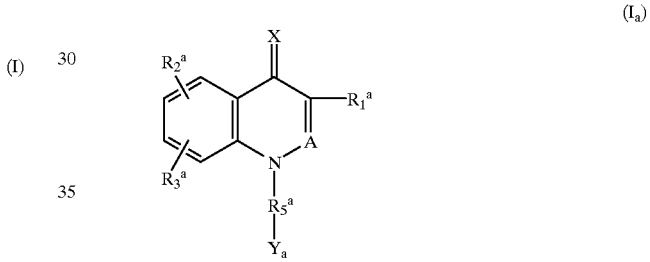

(I$_a$)

wherein R$_{1a}$ is selected from the group consisting of methyl, ethyl, n-propyl, n-propenyl, n-butyl and butenyl, R$_{2a}$ and R$_{3a}$ are individually selected from the group consisting of hydrogen, halogen, hydroxyl, mercapto, cyano, nitro, benzoyl, acyl of 1 to 6 carbon atoms, sulfo, carboxy free, salified or esterified by alkyl of 1 to 4 carbon atoms, tetrazolyl, alkyl, alkoxy and alkylthio of 1 to 6 carbon atoms, phenyl, naphthyl, benzyl and phenylthio, all being optionally substituted by at least one member of the group consisting of halogen, hydroxyl, alkoxy of 1 to 4 carbon atoms, trifluoromethyl, cyano, free, salified and esterified carboxy, tetrazolyl and isoxazolyl, amino, mono- or dialkylamino, carbamoyl, A$_a$ is nitrogen or C— R$_{4a}$, R$_{4a}$ is hydrogen, acyl of 1 to 6 carbon atoms, cyano, carboxy free, salified and esterified by alkyl of 1 to 4 carbon atoms, alkyl of 1 to 6 carbon atoms optionally substituted by at least one hydroxyl or halogen, X is oxygen or sulfur, R$_5$ is a divalent alkylene of 1 to 4 carbon atoms, Y$_a$ is phenyl or biphenyl optionally substituted by at least one member selected from the group consisting of hydroxyl, halogen, alkyl and alkoxy of 1 to 4 carbon atoms, trifluoromethyl, cyano, nitro, free, salified and esterified carboxy, tetrazole and isoxazole.

4. A compound of claim 1 wherein Y$_B$ is phenyl or biphenyl unsubstituted or substituted with a member selected from the group consisting of —CN, carboxy, tetrazolyl and alkyl and alkenyl, both optionally substituted with carboxy.

5. A compound which is 3-butyl-7-[(1-pyrrolidinyl)-carbonyl]-1-[(2'-(1H-tetrazol-5-yl)-1-(1,1'-biphenyl)-4-yl)-4-yl-methyl]-4-4(1H)-quinolinone.

6. A method of treating cardiovascular illness comprising administering to warm-blooded animals an amount of at least one compound of claim 1 to treat cardiovascular illness.

7. A method of treating cardiovascular illness comprising administering to warm-blooded animals an amount of at least one compound of claim 3 to treat cardiovascular illness.

* * * * *